United States Patent
Osvath et al.

(10) Patent No.: US 9,200,947 B2
(45) Date of Patent: Dec. 1, 2015

(54) IMAGING MODALITY USING PENETRATING RADIATIONS

(76) Inventors: Szabolcs Osvath, Budapest (HU); Krisztián Szigeti, Budapest (HU)

(*) Notice: Subject to any disclaimer, the term of this patent is extended or adjusted under 35 U.S.C. 154(b) by 33 days.

(21) Appl. No.: 13/807,950

(22) PCT Filed: Jun. 29, 2011

(86) PCT No.: PCT/IB2011/001522
§ 371 (c)(1),
(2), (4) Date: Jan. 16, 2013

(87) PCT Pub. No.: WO2012/001496
PCT Pub. Date: Jan. 5, 2012

(65) Prior Publication Data
US 2013/0112874 A1    May 9, 2013

Related U.S. Application Data

(60) Provisional application No. 61/360,524, filed on Jul. 1, 2010.

(51) Int. Cl.
*G01T 1/24* (2006.01)
*G01J 1/02* (2006.01)
(Continued)

(52) U.S. Cl.
CPC . *G01J 1/02* (2013.01); *A61B 6/486* (2013.01); *A61B 6/5205* (2013.01);
(Continued)

(58) Field of Classification Search
CPC ............... G01N 23/083; G01N 23/04; G01N 2223/076; G01N 2223/419; G01N 23/02; H05G 1/60; A61B 6/486; A61B 6/5202; A61B 6/5282; G06T 11/006; G06T 2211/412; G21K 7/00; H01J 2237/2813

USPC ..................................................... 250/370.08
See application file for complete search history.

(56) References Cited

U.S. PATENT DOCUMENTS 3,778,614 A * 12/1973 Hounsfield ............... 378/11
3,924,131 A * 12/1975 Hounsfield ............... 378/11
(Continued)

FOREIGN PATENT DOCUMENTS

| EP | 1 959 397 A2 | 8/2008 |
| WO | 03/071483 A2 | 8/2003 |
| WO | 2007/074467 A2 | 7/2007 |

OTHER PUBLICATIONS

Authors: Elisabeth A. Ring and Niels de Jonge, Title: Microfluidic System for Transmission Electron Microscopy, Date: 2010, Publisher: Microscopy Society of America.*
(Continued)

*Primary Examiner* — David J Makiya
*Assistant Examiner* — Taeho Jo
(74) *Attorney, Agent, or Firm* — Young & Thompson

(57) ABSTRACT

Systems and methods which use penetrating radiation to obtain novel type of information about objects of interest. This information may be represented as novel type of image. In the present embodiments, penetrating radiation is directed through the object of interest. The attenuated radiation emerging from the object of interest is detected by at least one detector. A plurality of measurements is collected. At least one statistical parameter describing variations of the measurements may be calculated and used for reconstructing an image representing fluctuations of the attenuation of the penetrating radiation in the object of study. At least one other statistical parameter representing the mean attenuation image, the error of the fluctuation image, or the error of the mean attenuation image may also be calculated and used to reconstruct images of the object of interest.

27 Claims, 10 Drawing Sheets

(51) Int. Cl.
  *A61B 6/00* (2006.01)
  *G06T 11/00* (2006.01)
  *G21K 7/00* (2006.01)

(52) U.S. Cl.
  CPC ............ *A61B 6/5282* (2013.01); *G06T 11/006* (2013.01); *G06T 2211/412* (2013.01); *G21K 7/00* (2013.01); *H01J 2237/2813* (2013.01)

(56) References Cited

U.S. PATENT DOCUMENTS

| | | | |
|---|---|---|---|
| 4,123,654 A * | 10/1978 | Reiss et al. | 378/87 |
| 4,278,888 A * | 7/1981 | Wagner | 378/20 |
| 5,055,789 A * | 10/1991 | Kondo et al. | 324/309 |
| 5,493,596 A * | 2/1996 | Annis | 378/57 |
| 6,169,817 B1 | 1/2001 | Parker et al. | |
| 6,256,403 B1 | 7/2001 | Florent et al. | |
| 6,421,552 B1 | 7/2002 | Hsieh | |
| 6,535,570 B2 | 3/2003 | Stergiopoulos et al. | |
| 6,747,697 B1 * | 6/2004 | Lin et al. | 348/246 |
| 6,754,298 B2 | 6/2004 | Fessler | |
| 6,879,656 B2 | 4/2005 | Cesmeli et al. | |
| 7,085,342 B2 | 8/2006 | Younis et al. | |
| 7,103,204 B1 | 9/2006 | Celler et al. | |
| 7,187,794 B2 | 3/2007 | Liang et al. | |
| 7,297,958 B2 * | 11/2007 | Kojima et al. | 250/370.09 |
| 7,356,174 B2 | 4/2008 | Leue et al. | |
| 7,711,089 B2 * | 5/2010 | Boyden et al. | 378/87 |
| 7,759,646 B2 * | 7/2010 | Amemiya et al. | 250/363.04 |
| 8,000,773 B2 * | 8/2011 | Rousso et al. | 600/436 |
| 2005/0226484 A1 | 10/2005 | Basu et al. | |
| 2005/0249391 A1 | 11/2005 | Kimmel et al. | |
| 2006/0100510 A1 * | 5/2006 | Klausz | 600/429 |
| 2008/0042067 A1 * | 2/2008 | Rousso et al. | 250/363.04 |
| 2008/0253511 A1 * | 10/2008 | Boyden et al. | 378/21 |
| 2009/0078875 A1 * | 3/2009 | Rousso et al. | 250/363.04 |
| 2009/0116617 A1 * | 5/2009 | Mastronardi et al. | 378/87 |
| 2009/0201291 A1 | 8/2009 | Ziv et al. | |
| 2010/0027740 A1 * | 2/2010 | Adams et al. | 378/45 |
| 2010/0119032 A1 * | 5/2010 | Yan et al. | 378/4 |
| 2010/0320389 A1 * | 12/2010 | Tonami et al. | 250/361 |

OTHER PUBLICATIONS

Authors: Renu Sharma and Peter A. Crozier, Title: Environmental Transmission Electron Microscopy in Nanotechnology, Publisher: Electron Microscopy.*

International Search Report, dated Dec. 30, 2011, from corresponding PCT application.

Chien-Min Kao et al., "Image Reconstruction for Dynamic PET Based on Low-Order Approximation and Restoration of the Sinogram", IEEE Transactions on Medical Imaging, Dec. 1997, pp. 738-749, vol. 16, No. 6.

Miles N. Wernick et al., "Fast Spatio-Temporal Image Reconstruction for Dynamic PET", IEEE Transactions on Medical Imaging, Mar. 1999, pp. 185-195, vol. 18, No. 3.

* cited by examiner

A

B 908
910

904  906  902

A     B

1010

IMAGING MODALITY USING PENETRATING RADIATIONS

FIELD OF THE INVENTION

This invention pertains to imaging equipment, and more particularly to a system and method for imaging fluctuations in the attenuation of penetrating radiation in an object or living creature.

BACKGROUND OF THE INVENTION

Several types of radiation have the ability to penetrate through objects or the body of living creatures. Properly used, these radiations offer non invasive techniques to create an image of the internal structure of different objects of interest, like non-living articles or living bodies. Any penetrating radiation can be used for attenuation-based imaging, if technical solutions to generate, collimate, guide and detect the radiation are available. Probably the most widely used penetrating radiation is x-ray. Other imaging methods may use the attenuation of gamma radiation, visible light, infrared radiation, terahertz radiation, ultrasound, electron beams or ion beams, and further development in this area can be expected. A few of the techniques utilizing these radiations are already well established, while a few are still being developed.

Attenuation-based imaging techniques work by projecting beams of a penetrating radiation through an object of interest. The radiation is generated by a radiation source, and beams of the radiation are usually focused or collimated before passing through the region of the object to be imaged. The radiation is attenuated by the object of interest, and a shadow image (projection) of the region of interest is formed. To record the image, intensity of the emerging attenuated radiation can be detected by a detector, or set of detector elements. These detectors convert the intensity reading into a signal, which can be electronically processed. The image representing the distribution of absorption inside the object of interest can be reconstructed from the recorded intensities.

FIG. 1 (prior art) shows the basic idea of the above image formation process in a flowchart.

Step 102 includes the determination of the attenuation of a penetrating radiation in an object of interest along at least one projection line.

Step 106 includes the reconstruction of the spatial distribution of the attenuation of the object in a viewable image.

Such a simple data acquisition procedure, however, does not allow for the accurate determination of the error of the measured image nor the estimation of the variability of the attenuation inside the body.

One interesting imaging method which uses electron beam as the penetrating radiation is electron microscopy. The transmission electron microscope uses electromagnetic "lenses" to control the electron beam. The electron beam is passed through a specimen and projected on an electron detector to record the shadow image of the specimen. Electron microscopes are used in the study of a broad range of organic specimens including biological specimens such as microorganisms, cells, large molecules, biopsy samples, and of inorganic specimens, including metals and crystals. Environmental electron microscopy is an electron microscopy technique that offers the advantage of visualizing biological samples in their native hydrated state.

Projection images obtained using x-rays (radiographs) have been used in various fields since the discovery of x-rays. For many industrial, medical or research applications recording an x-ray shadow along one projection direction may be enough. In many uses, however, a more detailed three dimensional image of the object of interest may be desirable. Computed tomography (CT) combines several projections recorded from different directions (angles of view) to produce cross section images of the object of interest. The cross section images can be used to reconstruct a 3D image of the object of study. The created 3D or cross section images are typically visualized on a computer screen, printed, or reproduced on a film.

Computed tomography is widely used in industry, research and also in medical imaging. In medical applications, the difference of the absorbance of different tissues gives enough contrast for the adequate diagnosis in many cases. If the contrast between different tissues is not enough, contrast agents are used to facilitate the examination.

To describe the absorption and detection of different radiations it may be useful to think about radiation as particles. The particles of the electromagnetic waves are called photons. In the case of electron or ion beams the particle nature of the radiation is more obvious. The radiation intensity falling on a detector is proportional to the number of particles reaching the detector in unit time. The particle count reading of a detector, however, may vary even if the intensity falling on the detector is constant. The actual number of counted particles fluctuates around an average according to Poisson distribution resulting in the so called shot noise. This effect introduces a theoretically unavoidable inaccuracy in the intensity measurements of several penetrating radiations. Further error of the measured values can be caused by other factors, such as instrument noise. Depending on radiation type, and the contribution of different noise sources, the resulting measurements can have different distribution around a mean value. Poisson and Gaussian (normal) distributions were shown to occur in many cases.

Several prior art patent documents try to identify motions in acquired projections. The aim of these works is to find projections which are recorded in a specific phase of the motion (U.S. Pat. No. 7,085,342 to Younis et al.), to remove motion artifacts from the images (U.S. Pat. No. 6,535,570 to Stergiopuolos et al., U.S. Pat. No. 6,879,656 to Cesmeli et al.), or to calculate physiologically interesting characteristics of the heart (U.S. Pat. No. 6,421,552 to Hsieh). All the techniques taught in these prior art documents are limited to extracting a few characteristics of a periodically moving organ and produce motion artifact corrected series of still images.

Other prior art patent documents aim at minimizing the effect of the measurement error on the reconstructed image. One advantage of better image quality is the possibility of reducing the radiation dose used in imaging. Often, the published methods of the prior art allow an estimation of the error of the image as well. The disadvantage of these prior art methods, however, is that they are based on theoretical estimations of the variability of the measured data, rather than on a direct measurement.

In U.S. Pat. No. 7,356,174, Leue and coworkers describe a method to estimate the effect of the inaccuracy of the x-ray detection on a reconstructed image. The method described in this patent suffers from several shortcomings. The method is designed only for situations in which the imaged x-ray densities are time independent, and assumes that measured photon counts follow Poisson distribution. The method of Leue and coworkers is not able to reconstruct the image of any attenuation fluctuations of the object. In fact, such attenuation changes may lead to less accurate image reconstruction by the above method, and/or less accurate estimation of the error of the image.

In U.S. Pat. No. 7,187,794, Liang and coworkers describe a method for treating noise in low-dose computed tomography applications. After analyzing repeatedly recorded phantom scan datasets, Liang et al. conclude that in their case the noise is close to a normal distribution. Using the information acquired in the absence of a patient, this group proposes a means to lower the effect of noise on the reconstructed image of the patient. The method of Liang and coworkers is designed to image static structures, thus it can not visualize motions or fluctuations in the x-ray attenuation. Moreover, image reconstruction may become less reliable in the presence of such changes of attenuation.

The method published by Fessler (U.S. Pat. No. 6,754,298) reconstructs an image from a plurality of projection data recorded at different x-ray photon energy distributions. Similarly to the two patents described above, this technique also assumes a static object of study, and the gained image may deteriorate if this assumption is violated.

In U.S. Pat. No. 7,103,204, Celler and coworkers publish a method to track changes in the photon emission of an object. Their main purpose, however, is to represent movements as a series of image frames, rather than to determine the extent of movements in the pixels. Also, the method works on emission-based imaging techniques, and not transmission measurements.

In U.S. Pat. Appl. No. 2005/0,226,484, Basu and coworkers publish a method to estimate the variance of generated 3D CT images. Their method starts from the assumption that the variance originates only in the noise of the measurement which is dominated by the photon shot noise. As a consequence of this assumption, the method described in U.S. Pat. Appl. No. 2005/0,226,484 is incapable of generating images representing the attenuation fluctuation of the object of interest.

Many image processing methods (e.g. U.S. Pat. No. 6,256,403 to Florent and coworkers) calculate the pixel variance of images from the neighborhood of the given pixel. The result of such calculations reflects the variance of the image along the space coordinates in a certain region, and can not represent time dependent fluctuations.

In U.S. Pat. No. 6,169,817, Parker and coworkers describe a method of 4D (space and time) visualization of image data. Spatial (regional) variance is calculated for individual image frames to determine connectivity of pixels in the image. Temporal changes are represented as a series of consecutive still images. This method is also incapable to represent attenuation fluctuations.

Patent No. EP 1,959,397 to O'Halloran and coworkers focuses on the removal of motion artifacts from images. The method uses HYPR reconstruction to represent the imaged object as a snapshot taken at different times during the motion. This method focuses on removal of motion artifacts to generate still images, and it is not designed to represent local fluctuations.

SUMMARY OF THE INVENTION

The principle objective of the invention is to provide a new imaging modality which may represent internal motions or fluctuations of at least one imaged object of interest. The object of interest may be a non-living article, or living creature, or part of an article or part of living creature. Internal motions may be imaged by the analysis of the associated fluctuations in the attenuation of a penetrating radiation.

A further objective of the invention is to allow a more accurate reconstruction of the mean attenuation image and give a better estimation of the error of the reconstructed images.

In one embodiment the present invention provides for a method for imaging an object of interest using penetrating radiation, characterized in that said method comprises: (a) providing a plurality of measurements of the penetrating radiation passing through the object of interest along at least one direction of detection; (b) processing the plurality of measurements to obtain at least one statistical parameter capable of describing a width of a temporal distribution of the plurality of measurements for each direction of detection; (c) and reconstructing the image of the object of interest based on the at least one parameter describing the distribution of the plurality of measurements, thereby obtaining images of the object of interest.

In another embodiment the present invention provides for an image processing method for determining relative movement of structures within an object of interest, characterized in that said method comprises: (a) providing a plurality of measurements of a penetrating radiation through the object of interest along at least one direction of detection; (b) processing the plurality of measurements to obtain at least one parameter which describes a fluctuation of the plurality of measurements for each of the at least one direction of detection; (c) and reconstructing an image of the object of interest based on the at least one parameter, wherein said reconstructed image based on the fluctuation of the plurality of measurements provides information on the relative movement of structures within the object of interest.

In another embodiment the present invention provides for a system for reconstructing an image of an object of interest characterized in that said system comprises: (a) a source capable of substantially emitting penetrating radiation; (b) a detector sensitive to said penetrating radiation, said detector capable of producing a plurality of measurements related to the penetrating radiation passing through the object of interest; (c) a processor means having at least one algorithm for calculating at least one statistical parameter capable of describing a width of a temporal distribution of the plurality of measurements for each direction of detection; and (d) an image reconstruction processor means for reconstructing the image of the object of interest based on the at least one parameter describing the distribution of the plurality of measurements.

BRIEF DESCRIPTION OF THE DRAWINGS

The invention will be described with reference to the embodiments shown in the drawings. It should be understood that the intention is not to limit the invention only to the particular embodiments shown, but rather to cover all alterations, modifications and equivalent arrangements possible within the scope.

The invention will now be described in more detail, by way of example only, with reference to the accompanying drawings, in which.

DETAILED DESCRIPTION OF THE INVENTION

Overview

Disclosed herein, in one embodiment, is a new imaging modality capable of representing relative internal motions of imaged objects of study through the associated fluctuations in the attenuation of penetrating radiation.

Figure 1:
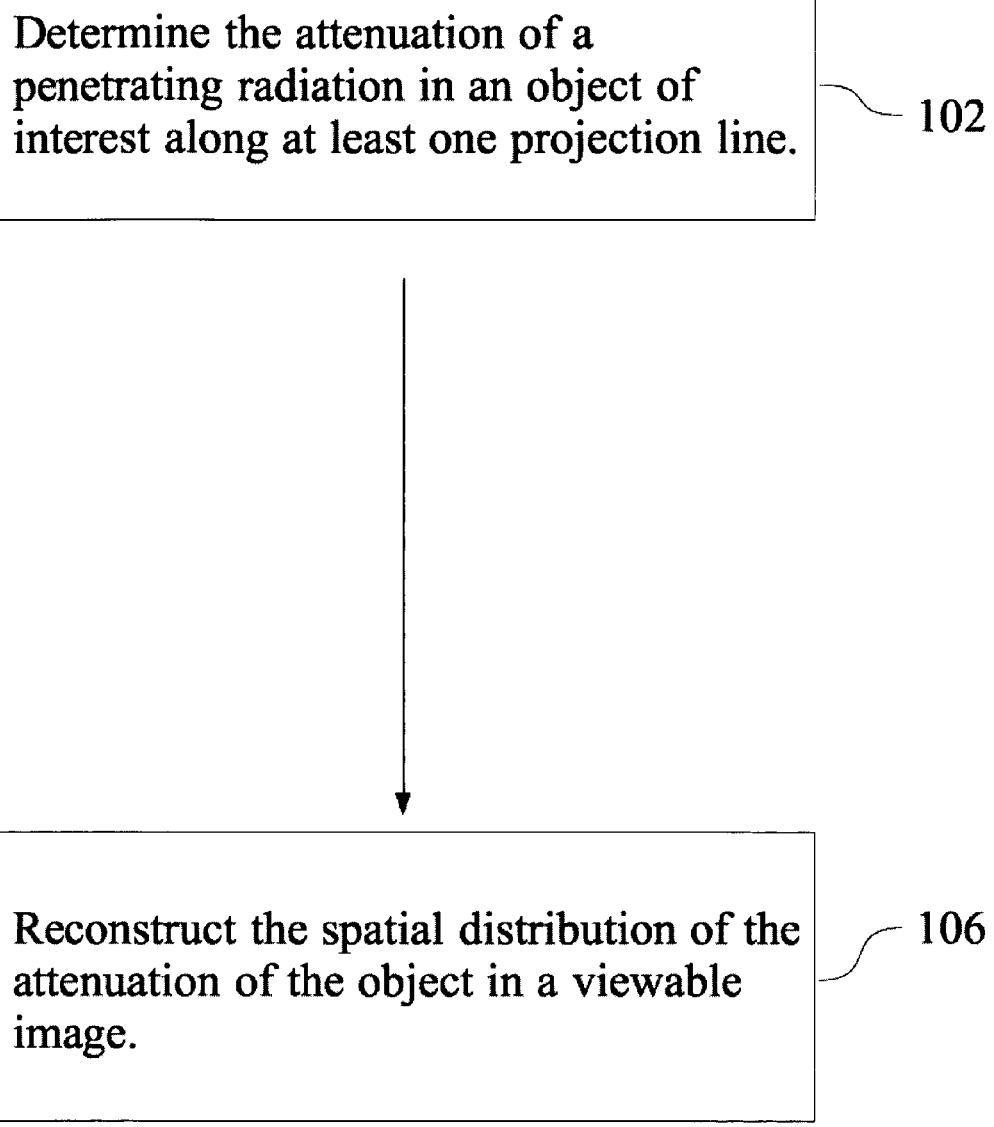
FIG. 1 is a flow chart of data acquisition and image reconstruction of the prior art.
Figure 2:
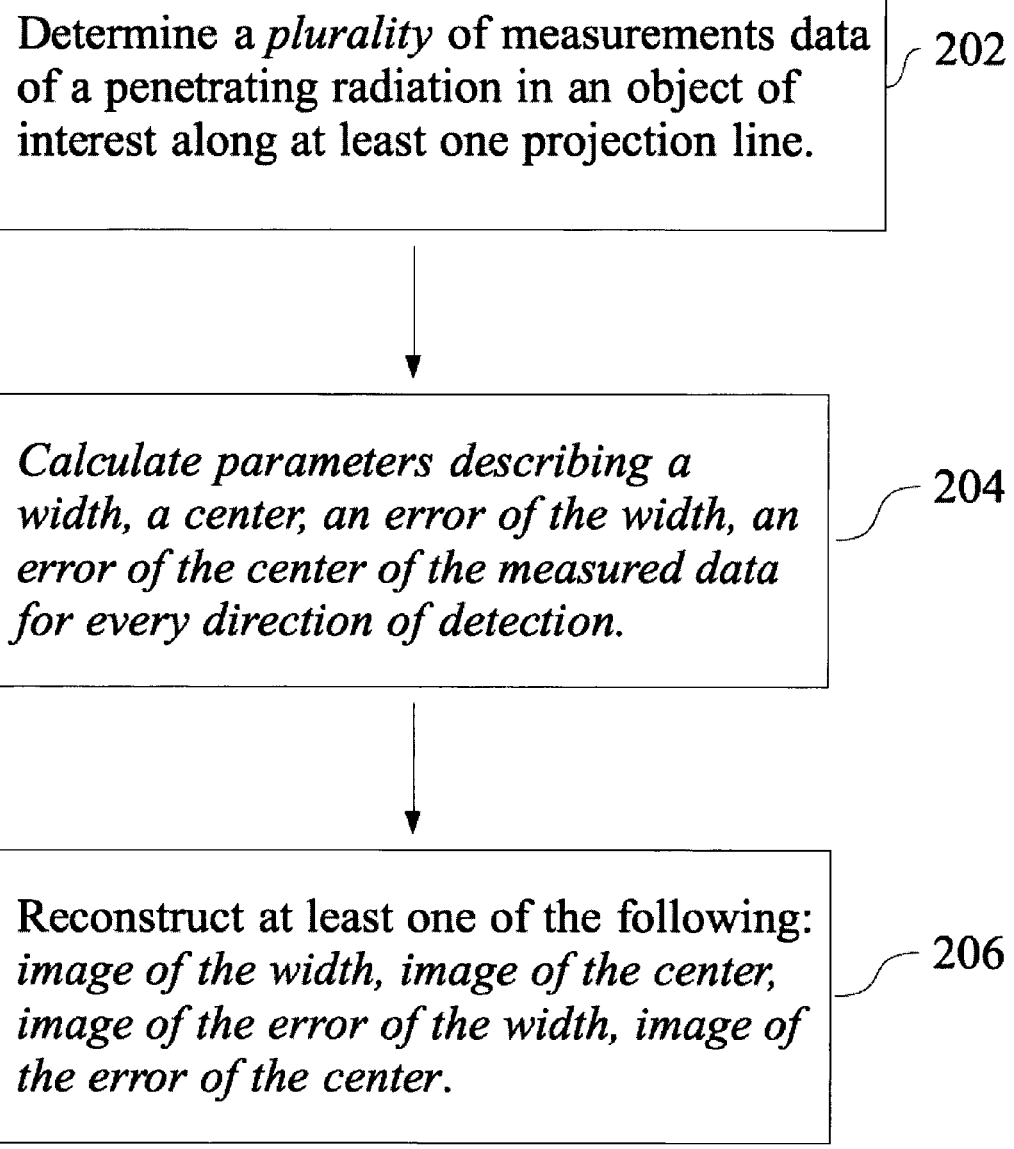
FIG. 2 is a general flowchart of data acquisition, processing and image reconstruction according to one embodiment of the present invention.

FIG. 2 is a flowchart of data acquisition, data processing and image reconstruction according to one embodiment of the present invention. A comparison between the flowchart represented in FIG. 2 to the one show in FIG. 1 (prior art) illustrates changes in data acquisition and analysis as well. In the embodiment of FIG. 2, a plurality of measurements using a penetrating radiation in an object of study may be collected along at least one projection line. Temporal distribution of the collected plurality of measurements may be characterized by the calculation of any suitable statistical parameters. The statistical parameter may then be used for the reconstruction of images describing the calculated temporal distribution of the penetrating radiation in the object of study. In one embodiment of the present invention, the statistical parameter may describe the width of the temporal distribution of the measurements. In another embodiment of the present invention, the statistical parameter may describe the center of the temporal distribution of the plurality of measurements. In another embodiment, the statistical parameter may describe the error of a statistical parameter describing the temporal distribution of the plurality of measurements. For example, the statistical parameter which may describe the width of the temporal distribution of the measurements may include, without limitation, a variance, a standard deviation, expected deviation, average absolute deviation or a moment of the distribution of the measurements obtained using the penetrating radiation. The statistical parameter which may describe the center of the temporal distribution of measurements may include, without limitations, an average, a mode, a mean or an expected value of the plurality of measurements. An error of all the parameters mentioned in this paragraph may also be used for the reconstruction of images.

In embodiments of the present invention, the plurality of measurements may be related to the intensity of the penetrating radiation passing through the object of study. For example, the plurality of measurements may include, without limitation, attenuation measurements of the penetrating radiation through the object of study or the electric field strength of the penetrating radiation through the object of study.

Example of penetrating radiation that may be used with the present invention, include, without limitation, electron beams, gamma radiation, infrared radiation, infrasound, ion beams, microwaves, radio waves, shock waves, sound, terahertz radiation, ultrasound, ultraviolet radiation, visible light or x-rays.

Various changes may be made in the embodiments and operating methods presented below without departing from the spirit or scope of the invention. All matter contained in the descriptions or shown in the accompanying drawings should be interpreted as illustrative and not in a limiting sense.

Applications

The invention disclosed herein may have several applications, a few of which may be described below. The descriptions provided herein below are for illustrative purposes only, and should not be taken as limiting the scope of the invention.

Fluctuation imaging of deformations of the object of interest may be of particular importance. The object of interest may be agitated by sound, ultrasound, shock waves, pressure, etc, and the resulting internal fluctuations recorded.

Fluctuation imaging of the deformations may provide information about weaknesses of manufactured or built structures. In such way the weaknesses may be discovered before any cracks of measurable size weaken the structure. The imaging methods provided herein may be particularly useful if failure of the structure risks the life or health of humans, or may cause costly damages.

Fluctuation imaging may also be used to map the deformability of the object of interest. This may be important in many fields, including engineering and medical imaging. In these techniques, the object of interest may be exposed to mechanical stress, pressure waves, shock waves, vibrations, infra-sound, sound, or ultrasound while recording a fluctuation image. The method may give a new type of image contrast based on the elasticity of the different parts of the object of interest. This method may yield useful diagnostic images even if the inherent fluctuation or motion of different tissues and/or deposits can not be directly visualized in a fluctuation image.

Benefits

The invention disclosed herein may have many economical, technical and health care benefits. Described herein are a few uses and benefits of the invention for illustrative purposes only. These descriptions should not be taken as limiting the scope of the invention.

Imaging by penetrating radiations produces several tens of billions of dollars sale per year, and is constantly increasing. Penetrating radiations which may be used in medical imaging systems, including, without limitation, computed tomography, X-ray microanalysis, microtomography, electron microtomography, ion microscopy, testing electronics parts, etc.

One important field of imaging is medical imaging. Image quality may be important while radiation dosage in many applications has to be kept low. Often, contrast agents have to be used to improve image quality. The sale and use of contrast agents constitutes a several billion dollar market itself. In addition to this, the use of contrast agents may trigger unwanted reactions (for example allergic response), which may cause additional risks for the patient.

Existing imaging modalities have a very wide use in industry, medical diagnosis, healing and research. Resolution of imaging equipments is constantly improving. The smallest resolvable distance of modern environmental electron microscopes may be less than 1 nm, which is in the range of the size of molecules. Fluctuation images recorded in an electron microscope in accordance to one embodiment of the present invention thus may yield information about the relative molecular scale movement of the object of interest. The smallest resolvable distance for medical x-ray computed tomography may be as small as 0.2 mm, whereas the resolution of small animal computed tomography may be 0.05 mm. This is roughly the size range of single cells. X-ray computed tomography fluctuation images obtained in accordance to the present invention may thus reflect the relative cellular movements of tissues.

Due to the high spatial resolution of medical x-ray computed tomography, relative movements at the cellular level may become visible, which may have an impact in the diagnosis of many diseases as well as planning, monitoring and controlling treatment. At present, x-ray computed tomography is too slow for direct tracking of many movements. Also, repeated imaging of the human body could result in higher radiation doses and higher associated health risks.

One aim of the invention disclosed herein may be to introduce a new imaging modality. This new modality may be able to record and analyze fluctuations of the attenuation of penetrating radiation in an object of interest. Another aim of the present invention may be to provide a new and better estimation of the average attenuation image and of the inaccuracy of the average attenuation image.

The disclosed new methods of the present invention may not require the use of higher doses of radiation. The amount of radiation which may be used in present versions of imaging instruments (or even less) may be split in a plurality of measurements, to record a plurality of readings. Readings may than be used to determine both the width of the readings or the expected value of the readings (or average, or sum, or any equivalent statistical parameter) as before.

The disclosed invention may prove useful in several ways. The new imaging modality of the present invention may give access to new type of information not available up to now. The new imaging modality of the present invention may also show new material contrast schemes allowing better visualization of structures. The invention may allow for a better estimation of the average attenuation image, and it may also make possible a better estimation of the error of the average attenuation image. These advantages may be useful where penetrating radiations may be used for imaging.

In many fields of use, no new market for the present invention may need to be created. Customers interested in attenuation based imaging may find the more accurate estimation of the mean attenuation image, and the better estimation of the variance of the images obtained in accordance with the present invention useful. Also, earlier users of existing imaging modalities may not need extra training to be able to use the new imaging modality of the present invention.

The new imaging modality of the present invention may introduce new contrast schemes, which may allow new applications and may open new markets as well.

The new imaging modality of the present invention may require only minor modification of existing data acquisition modules and data processing procedures. This may have several advantages: i) the costs of the development necessary to integrate the new modality into presently manufactured equipment may be small; ii) manufacturing instruments in which the new modality has been integrated may not be more expensive than the present instruments lacking the new modality; iii) switching to manufacture instruments with the new modality incorporated may not need large changes in the production procedures; iv) modifications required for the new modality and new methods may inexpensively be added to imaging devices installed earlier. The new methods of the present invention thus may be installed for established customers as well.

A better estimation of the error of the image may also be used for better denoising of the average images. In medical imaging, a better estimation of the average image may yield better image quality, which may allow reduction of the exposure of patients to the radiation used for imaging. A better estimation of the error of the image may also help to optimize radiation intensity and measurement time necessary to get the diagnostic information. This, in turn, may help to avoid unnecessary patient doses. New material contrast schemes may also allow the reduction of the patient doses in cases where imaging is traditionally difficult due to low contrast between tissues.

New contrast schemes may also allow the use of double modality contrast materials. MRI contrast agents (such as Gd, or $Fe_nO_m$ compounds) may also serve as contrast agents for the x-ray fluctuation detections. The use of such dual contrast agents may reduce the need of contrast agents in dual modality MRI and X-ray CT measurements, or improve the X-ray image quality without the use of extra contrast materials.

Fluctuation images may find several important applications in the field of medical computed tomography. Different tissues may show a different extent of movement and fluctuation. These movements may also have a different time-course. Faster dividing tissues may show more fluctuations, while non-living deposits may be virtually still. An image showing the extent or the speed of fluctuations may thus be used effectively to diagnose several diseases.

For example, fluctuation attenuation images obtained in accordance with the present invention may have several advantages over recording only the mean attenuation image. Fluctuation images may be less sensitive to the presence of relatively high background attenuations. In images representing only the mean attenuation, features giving a small modulation of the mean attenuation may not be discernible if a high background attenuation is present. Fluctuation images may remove the mean background and may allow visualizing parts, which may give a small fluctuating contribution. The proposed new imaging modality of the present invention thus introduces a new, fluctuation-based contrast. Better contrast may result in better image quality and a possibility to lower the patient dose. Introducing the new modality thus may decrease the risks of the examination.

Cancer is one major cause of human death. It caused about 13% of the deaths in 2007, which means that 7.6 million people dyed of cancer in that year. Early diagnosis of cancer is vital to the successful treatment. Although methods for diagnosing cancer exist, a better and/or independent method could give higher diagnostic sensitivity, and thus higher treatment success. Cancer tissues divide faster, and contain more blood vessels than healthy ones. With appropriate timing of the data acquisition this may also mean larger fluctuations. These differences between cancer and healthy tissues may be used as a diagnostic signature of tumors in fluctuation images.

Inflammation is the response of the vascular and the immune system to infections. In autoimmune diseases inflammation attacks the patients own tissues. Both in healthy and in pathologic inflammations it is important to identify and localize the inflammation. Inflammations have a higher metabolic rate, with more blood flow and the presence of more immune cells. All these may cause that inflammations have a distinct signature in the fluctuation images.

Approximately two dozen human diseases have been linked to the formation of ordered insoluble protein aggregates called amyloid. Amongst the diseases linked to the formation of such amyloid plaques are Creutzfeldt-Jacob disease (the human variant of mad cow disease), Alzheimer disease, Parkinson disease, and type II diabetes. At present there is no method for visualizing or tracking the deposition of amyloid plaques. Diagnosis of the amyloid related diseases happens in a later phase, when the symptoms already become visible. Amyloid plaques are inert non-living inclusions. In a fluctuation image these plaques may show up as motionless bodies, thus giving a marker for their identification. Even though the plaques and the surrounding tissue look the same in the images representing the mean of the attenuation, they may clearly separate in the fluctuation images.

Above we explained in more detail the possibility of diagnosing amyloid related diseases, but the benefits described in the above paragraph may be used for the diagnosis of any non-living material inside the body. These include, but are not limited to the visualization of any stent, stone, plaque, deposit or inclusion, in any part of the body.

Obtaining an image of blood vessels with suitable contrast traditionally requires the injection of contrast agents into the bloodstream. Blood is a fluid tissue with a variety of cells with different sizes flowing in the blood vessels. As the cells move with the bloodstream, they cause a fluctuating density in the recorded projections. In a fluctuation image the blood flow may thus be directly visualized without the use of contrast agents. The periodic pumping of the heart may also periodically move the wall of the blood vessels, which may give a sharper contrast of the walls of the vessels in the fluctuation image.

Figure 9:
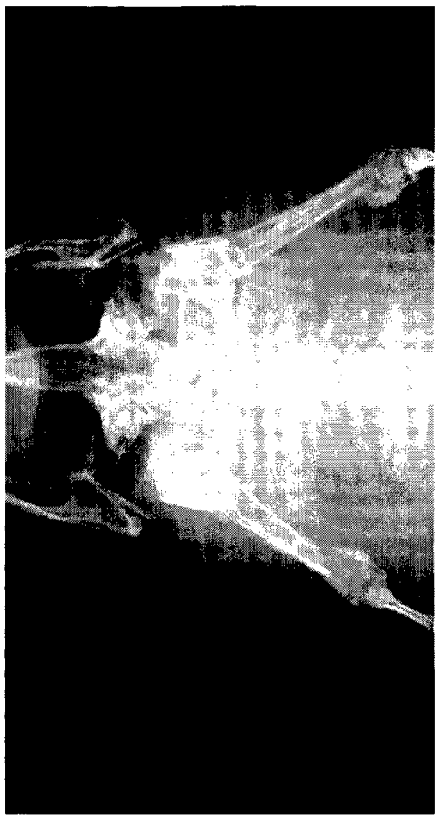
FIG. 9A is an exemplary projection average density image of the chest of a frog obtained with the embodiment described in FIG. 5.
FIG. 9B is an exemplary projection variance density image of the chest of a frog obtained with the embodiment described in FIG. 5.
Figure 9:
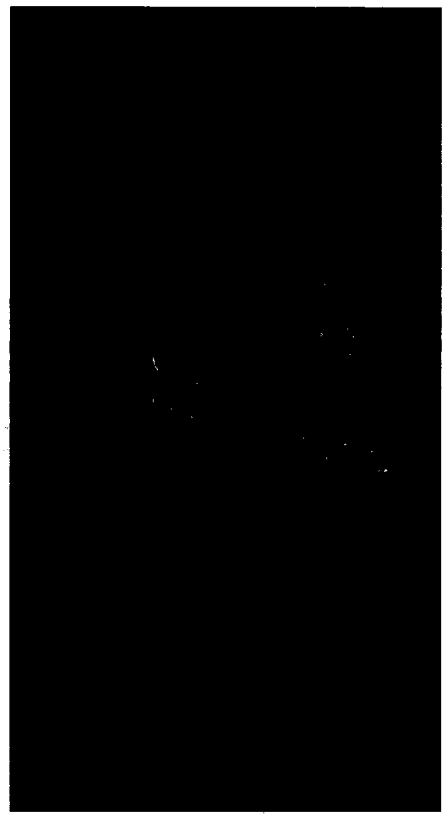
Figure 10:
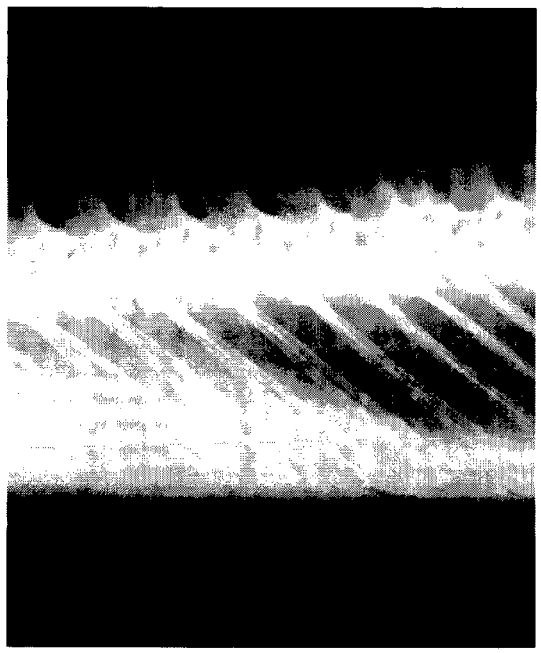
FIG. 10A is an exemplary projection average density image of part of a snake, containing the heart, obtained with the embodiment described in FIG. 5.
FIG. 10B is an exemplary projection variance density image of part of a snake, containing the heart, obtained with the embodiment described in FIG. 5.
Figure 10:
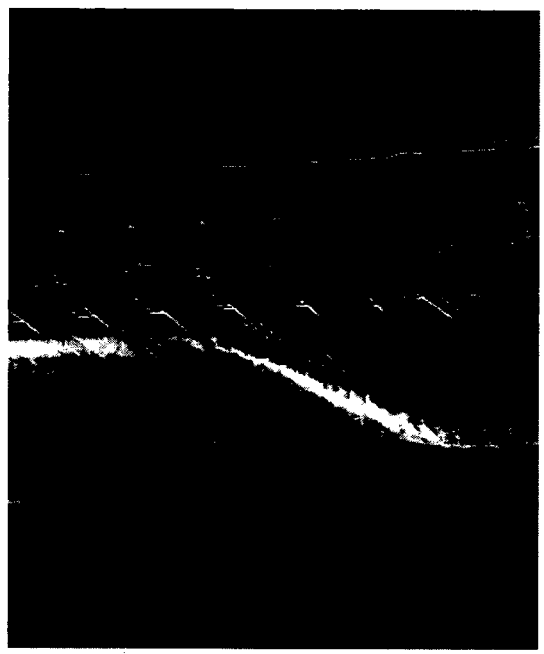

Fluctuation imaging of the heart, lungs, or other moving organs may also be possible, as illustrated in FIGS. 9 and 10. The method of the present invention would not represent the movement as a series of sharp still images. The method of the present invention may be able to determine the fluctuation of the attenuation in every point. The methods of the present invention may yield useful diagnostic information, and it may also need less radiation exposure.

As shown in the above examples, the new imaging modality of the present invention may advance diagnosing several types of diseases, like cancer, conditions of the vascular system, autoimmune diseases, amyloidoses, and so forth. For many of these there is a high and increasing demand due to the aging population of the western societies. For some of these conditions there is no diagnostic method at present, so the new modality may not have competing alternatives.

Fluctuation images may also be used in imaging of several physical phenomena or engineering processes including but not limited to the ones listed below.

Fluctuation images may be used in identifying regions which have different x-ray density than their environment while the object of study may be moved on a production line. Imaging of fluctuations may prove useful in characterizing the movement or explosion of fuel in engines. Fluctuation images may give better insight in the movement of fluids in or around objects such as fans, turbines, wings, and so forth. Visualization of the flow may help a better optimization of the work conditions of engines, power plants, airplanes and so forth. Imaging of fluctuations may also help visualize fluctuations of electric discharges which may also contribute to optimization of spark gaps, motors, lamps, and so forth.

Several published methods aim to minimize the effect of the inaccuracy of the measurement on the reconstructed image. Here we provide a new method to estimate the inaccuracy of the average attenuation image as well. By handling better the variability of the measurements, our new method may yield better image quality.

This may allow reduction of patient dose in medical applications.

Other Embodiments

Variations or modifications to the design and construction of this invention, may occur to those skilled in the art upon reviewing this disclosure. Such variations or modifications, if within the spirit of this invention, are intended to be encompassed within this provisional patent application, as well as within the patent applications intended to be filed based on it, and the resulting patent protection issuing upon this invention.

Conclusions, Ramifications, and Scope

The description previously provided contains many specifications. These should not be construed as limiting the scope of the embodiments, but as merely providing illustrations of some of the presently preferred embodiments.

In all aspects of the present disclosure, penetrating radiation means any radiation or wave that is capable of penetrating through the studied object of interest. These may include, but are not limited to: x-ray, gamma radiation, visible light, infrared radiation, terahertz radiation, ultrasound, electron beams, ion beams, or shock waves.

In one embodiment, a plurality of detector readings may be use to get measurement information about the variation of the strength of the penetrating radiation. The plurality of measurements may be done in many ways. In a simplest case detection may be performed in a plurality of identical acquisition time intervals which may or may not be separated by inactive time periods in which the detector is not collecting data. Any other data acquisition pattern may also be successfully used if it produces a plurality of data for the subsequent calculation of the required statistical parameters. Such acquisition patterns may include, but are not limited to methods using detection and inactive periods of varying length, methods which record the impact time of individual particles, or methods which record the time between the impact of individual particles.

It should be understood that the term "measurement" would be not only the detector reading itself, but also any number or parameter calculated from the detector reading.

In the examples presented in this document the detector recorded the intensity of the penetrating radiation. Instead of intensity, other embodiments may use any other physical quantity indicating the strength of the radiation, including, without limitation photon number, electron number, ion number, pressure, pressure change, oscillation speed, electric field strength, or magnetic field strength, or any mathematical function of these quantities.

In the presented embodiments the detector unit records the strength of the penetrating radiation. Many other embodiments of the detector can be built which allow quantification of the intensity fluctuations. Such detection methods include, but are not limited to the use of electronic cards directly evaluating the variation of the signal, detectors that are sensitive to derivatives of the radiation intensity, modulation of detector sensitivity, or modulation of the intensity of the penetrating radiation.

Detector readings used for the evaluation of the intensity variations could be made with the same detector element, but this is not a necessary condition. Embodiments may be created which use different detectors or detector elements to gather information about the variation of the intensity of the radiation. Presented embodiments used intensities measured along the same line to determine fluctuations of the object of study. It is contemplated that intensity readings along different lines may also be used for the reconstruction of the mean attenuation and fluctuation images.

Images representing fluctuations in time may also be produced by the reconstruction of a plurality of simple image scans and calculating the parameter describing time variance of the signal from the reconstructed images.

Presented embodiments determine at least one quantity describing the fluctuation of the attenuated intensity of the penetrating radiation. It should be understood that any quantity which relates to the attenuation of the radiation (transmission, absorption, extinction, extinction coefficient, attenuation coefficient, mass attenuation coefficient, half value thickness, transmitted intensity, any mathematical combination of these, and so forth) may also be used instead of the attenuation. Also, any parameter that may be used to describe the time course and/or size of the fluctuations is also suitable. Such parameters include, but are not limited to the variance, standard deviation, expected deviation, average absolute deviation, any moment or central moment of the distribution, characteristic time of the fluctuations, relaxation time of the fluctuations, Fourier components, and so forth.

One embodiment of the present invention takes into account the Poisson distribution of the photon counting instrument noise. This should not be understood as limiting the scope of the embodiments. This distribution is merely one example for the inherent variation of the detector readings, which may be observed in the absence of fluctuations inside the object of interest. We contemplate that other embodiments may take in account any other distribution of the inherent variation of the detector readings. The inherent random variation of the detector readings may be empirically determined, theoretically derived, or the result of a combination of the two. We also contemplate that in the case of larger intensities and more substantial attenuation fluctuations this correction may be altogether negligible.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

The examples are described for the purposes of illustration and are not intended to limit the scope of the invention.

Example 1

Environmental Transmission Electron Microscope System

Figure 3:
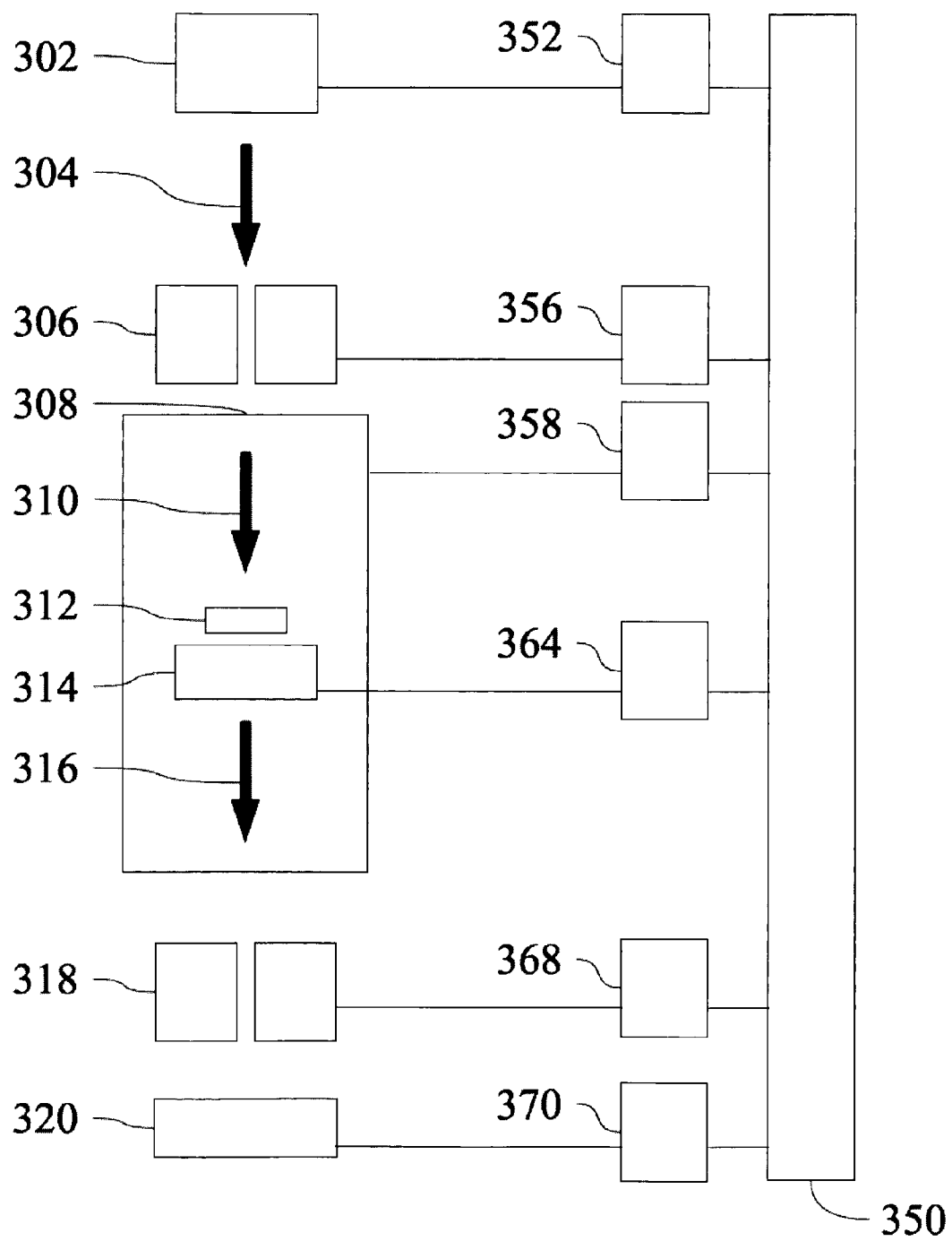
FIG. 3 is a diagram of a modified transmission electron microscope according to one embodiment of the present invention.

FIG. 3 illustrates a diagram of an environmental transmission electron microscope (ETEM) which may be capable of collecting measurements and reconstruct at least one image of at least one object of interest in accordance with one embodiment of the present invention. The ETEM uses electron beams as penetrating radiation to visualize the object(s) of interest. Other embodiments may use any other penetrating radiation including, but not limited to gamma radiation, infrared radiation, infrasound, ion beams, microwaves, radio waves, shock waves, sound, terahertz radiation, ultrasound, ultraviolet radiation, visible light. If other penetrating radiation is used, shaping of the radiation beam may require different elements (for example: collimator, lenses, electron optics, ion optics and so forth).

The embodiment presented in FIG. 3 may reconstruct at least one image of the object of interest based on any or several of the following: the average attenuation, the error of the average attenuation, the fluctuation of attenuation, and the error of fluctuation of attenuation of the penetrating radiation absorbance of the object of interest, or any other statistical parameter which may describe the temporal distribution of the collected measurements.

Instead of intensity, further embodiments may use any other physical quantity which may be related in any way to the intensity of the radiation, including, without limitation, electric field strength, magnetic field strength, photon number, electron number, ion number, pressure, pressure change, or oscillation speed. Other quantities which may be related to the intensity may also be used instead of intensity, such as transmission, absorbance different functions of intensity, and so forth.

The illustrated system of FIG. 3 includes an electron gun 302 emitting a beam of electrons 304. The electron gun 302 may be connected to an electron gun controller 352. The electron gun controller 352 may control the timing, intensity, and kinetic energy of the electrons used in imaging the object of interest.

The electron beam 304 may be passed through a condenser electron optics 306 before entering an environmental cell 308. The condenser electron optics 306 may be controlled by a condenser electron optics control system 356. The environmental cell 308 may be coupled to an environmental cell control system 358.

An electron beam 310 will reach a specimen (object of interest) 312. The object of interest 312 may be placed on a specimen stage 314 coupled to a specimen stage control system 364. The environmental cell 308 may provide a possibility to regulate the pressure and composition of the gas atmosphere around the object of interest 312 placed inside the environmental cell 308.

A portion of the electrons of the beam 310 may pass through and around the object of interest 312. The portion of the electrons which may pass through the object of interest may form an electron beam 316, which may fall on a detector 320. The electron beam which may pass through and around the specimen 312 may be focused on the electron detector 320 by a projection electron optics 318 which may be controlled by a projection electron optics control system 368. The detector 320 may include at least one element, which may be able to detect electrons. The detector 320 in this exemplary embodiment may be a CCD camera attached to a scintillating crystal. Other embodiments may use different image sensors instead of the CCD (for example photon-multiplier tube array, or CMOS sensors, and so forth).

In this embodiment, the detector 320 may be any detector which may be capable of detecting the impact of electrons. In this embodiment, the electron detector 320 may be controlled by an electron detector controller and data acquisition system 370.

In embodiments which may use other forms of penetrating radiation, the radiation may be detected with different detectors sensitive to the actual radiation used in the embodiment (for example photon multiplier, CCD camera, piezoelectric detector and so forth).

In the exemplary embodiment of FIG. 3, the electron detector 320 may produce electrical signals which may represent the attenuated intensity of the incident electron beams. In this embodiment, the electron detector controller 370 may receive analogue electrical signals from the detector 320 and may convert the analogue data to digital signals for subsequent processing by a computer means 350. An analogue to digital converter may also be incorporated in the detector, to obtain digital data from the detector. The intensity measurements detected by the detector 320 may be needed to reconstruct any image of the object of interest.

The electron gun control system 352, the condenser electron optics control system 356, the environmental cell control system 358, the specimen stage control system 364, the projection electron optics control system 368, as well as the electron detector control and data acquisition system 370 may be coupled to a computer 350.

In the described embodiment of FIG. 3 several control units may command the subunits of the ETEM to perform tasks connected to the data collection and processing. In one embodiment, a few or all of the controllers may be built of several units, performing some part of the tasks. In another embodiment several of the controllers may be grouped or integrated in larger units which may perform the control tasks of several or all of the mentioned control units. In one embodiment, instead of the computer 350, a combination of a plurality of general purpose and/or application specific digital computers may be utilized.

In the described embodiment of FIG. 3, different parts of the imaging equipment may communicate by electric signals, but connections may be done by several other methods. Any method suitable of transferring the necessary information may be used. For example, data may also be transferred by the means of optical cable, or wireless connection, and so forth.

The collected data may be transferred to the computer 350, and stored in the digital memory of the computer 350, or any storage device which may be part of, or coupled to the computer 350. Any type of memory capable of storing the collected data may be utilized. The memory may be local to the data acquisition system, or may include remote components. The computer may be local to the imaging device, or may be remote from it, coupled to the imaging device through a network, or other remote connection. The network may also be connected to a remote client or database. Acquired data, imaging parameters, reconstructed images may be visualized by many methods. These methods include, but are not limited to visualizing on screen, printing on paper, slide, or film.

The computer 350 may receive commands, settings and scanning parameters from an operator who controls the imaging system via input devices of the computer. The operator may observe the data or the reconstructed images, set input parameters, initiate imaging, and so forth. The operator may be local to the computer 350, or may be remote from it, coupled to the computer 350 through a network, or other remote connection. Some or all of the data processing described here may be performed remotely.

In this exemplary embodiment, the reconstructed image may visualize the internal structure of objects of interest which can be penetrated by electron beams.

Figure 4:
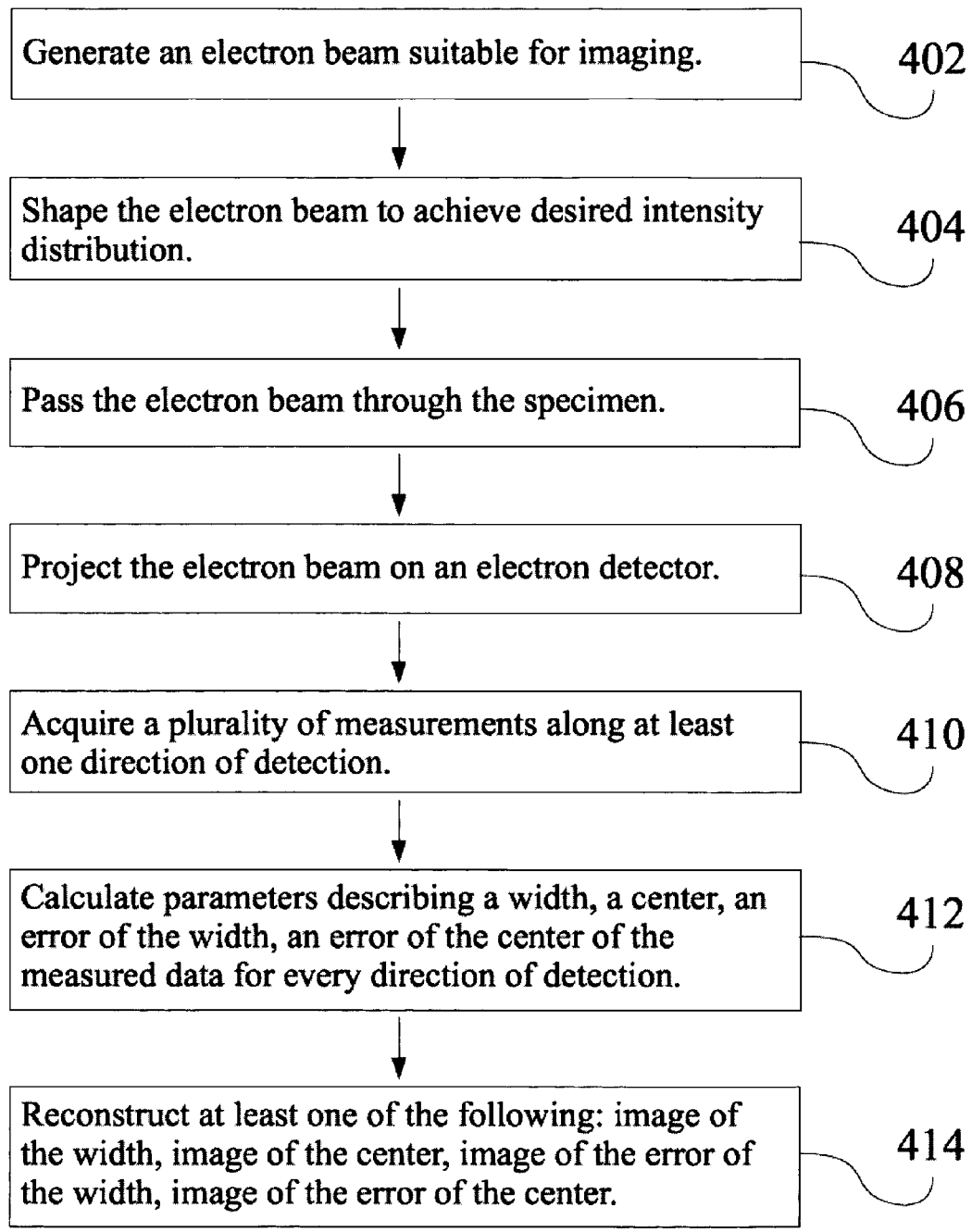
FIG. 4 is a flowchart of data acquisition, processing and image reconstruction using the transmission electron imaging system represented n FIG. 3.

FIG. 4 is a flowchart including exemplary steps for generating images reconstructed from statistical parameters describing the temporal distribution of the attenuated electron beam radiation passing through the object of study and captured by the detector, including, without limitation, the width of the temporal distribution of the attenuated electron beam, the center of the temporal distribution of the attenuated electron beam, and their respective estimated errors using the system described in FIG. 3.

In step 402 an electron beam 304 may be generated by the electron gun 302; the beam 304 may be shaped by the condenser electron optics 306 in step 404, and may be passed through the object of interest 312 in step 406. In step 408 the portion of the electron beam 316 which passed through the object of interest 312 may be projected on the detector 320 by the projection electron optics 318. In step 410 measurements representing intensity data along at least one direction may be collected. In step 412 at least one statistical parameter describing the temporal distribution of the collected measurements may be calculated. Examples of statistical parameters may include the average density, deviation of the density and their respective errors. In step 414 images representing the at least one statistical parameter describing the temporal distribution of the density of the electron beam in the object of interest 312 may be reconstructed.

As will be appreciated by those skilled in the art, intensity readings of the detector 320 may be subject to fluctuations. These fluctuations may be due to random noise of the measurement or to real changes in the attenuation of the penetrating radiation inside the object of interest 312. Random noise may come from the Poisson shot noise of the detection, from electronic noise of the detector, or attached electronics parts, etc. Random noise may have no information content about the object of interest 312. Fluctuations arising from real attenuation changes of the object of interest 312 may carry important information about the movements of the object of interest.

The described exemplary embodiment of FIGS. 3 and 4 is an ETEM which may create an image representing, for example, the average intensity of the electron beam and/or another image representing the fluctuation of the intensity.

In one embodiment, to determine the image of the object of interest 312, the presented embodiment may record the intensity I of the electron beam 316 passing through the object of interest 312 for every pixel of the image. Making a plurality of intensity detections for every pixel may reveal that the measured I intensity fluctuates.

If $I_0$ denotes the intensity of the electron beam before the absorber, I the intensity after the absorber, and D denotes the attenuation of the electron beam due to the absorber, then:

$$I = I_0 \cdot \mathrm{Exp}[-D] \tag{1}$$

Here Exp[. . .] denotes the e-based exponential function. The intensity I of the electron beam can be estimated by a detector that counts the electrons that fall on a given surface area in a given time interval.

In this embodiment it will be assumed that the attenuation D for the electron beam follows normal distribution due to movements. In such case the intensity I will follow lognormal distribution. In this embodiment it will also be assumed that the intensity measurement has a Poisson shot noise. Taking into account both sources of fluctuations the following expressions may be obtained for the expected value and variance of the detected electron numbers k:

$$E(k) = I_0 \cdot \mathrm{Exp}[\mathrm{Var}(D)/2 - E(D)], \tag{2}$$

$$\mathrm{Var}(k) = I_0 \cdot \mathrm{Exp}[\mathrm{Var}(D)/2 - 2 \cdot E(D)] \cdot (\mathrm{Exp}[D] - I_0 \cdot \mathrm{Exp}[0.5 \cdot \mathrm{Var}(D)] + I_0 \cdot \mathrm{Exp}[1.5 \cdot \mathrm{Var}(D)]) \tag{3}$$

If the expected value E(k) and variance Var(k) of the electron counts k are determined experimentally, the expected value E(D) and the variance Var(D) of the attenuation D may be calculated by solving the above equations:

$$E(D) = \text{Log}[I_0 \cdot \text{Sqrt}[\text{Var}(k) - E(k) + E(k)^2]/E(k)^2], \quad (4)$$

$$\text{Var}(D) = 2 \cdot \text{Log}[\text{Sqrt}[\text{Var}(k) - E(k) + E(k)^2]/E(k)] \quad (5)$$

where Log[ . . . ] denotes the natural (e-based) logarithm, Sqrt[ . . . ] denotes the square root function.

The expected value E(k) and variance Var(k) of the electron counts are parameters that describe the theoretical distribution of the counts k. These parameters can not be determined directly, but they can be estimated from measurements.

The presented embodiment may make a plurality (n) of electron count readings and may calculate an estimation for both the expected value E(k) and variance Var(k).

To estimate the error of the estimation of E(k) and Var(k) any statistical method (such as jackknifing, bootstrapping, and so forth) may be used which allows a reasonably accurate guess of the errors.

After estimation of the errors Err(E(k)) and Err(Var(k)), the expressions for the errors of the expected value E(D) and the variance Var(D) may be derived from the expressions for E(D) and Var(D). After simplifying the expressions, Err(E(D)) and Err(Var(D)) may be calculated the following way:

$$\text{Err}(E(D)) = (E(k)^2 - 1.855 \cdot E(k) + 2 \cdot \text{Var}(k)) \cdot \text{Var}(k)/(\text{Sqrt}[n] \cdot E(k) \cdot (E(k)^2 - E(k) + \text{Var}(k))), \quad (6)$$

$$\text{Err}(\text{Var}(D)) = (1.71 \cdot E(k) - 2 \cdot \text{Var}(k)) \cdot \text{Var}(k)/(\text{Sqrt}[n] \cdot E(k) \cdot (E(k)^2 - E(k) + \text{Var}(k))). \quad (7)$$

As described above, the presented embodiment may use a plurality of detector readings k to calculate an estimation for (1) the expected value E(D), (2) the variance Var(D), (3) the error of the expected value Err(E(D)), and (4) the error of the variance Err(Var(D)) of the density D. These four quantities may be represented as four different images.

The image of the expected value may represent information similar to conventional electron microscopy images.

The variance image may reflect the fluctuations of the object of interest. This new modality may be used to image relative movement of structures inside the object of study. The new modality may bring new contrast schemes, which may allow the visualization of structures which were not previously resolvable.

The error images hold information important for optimization of data acquisition, for efficient image analysis, denoising, automatic shape recognition, and so forth.

Other embodiments may be envisioned which may use different statistical parameters to describe the "typical" reading and/or width of the distribution of the measured data or of the attenuation D.

Example 2

Computed Tomography System

Figure 5:
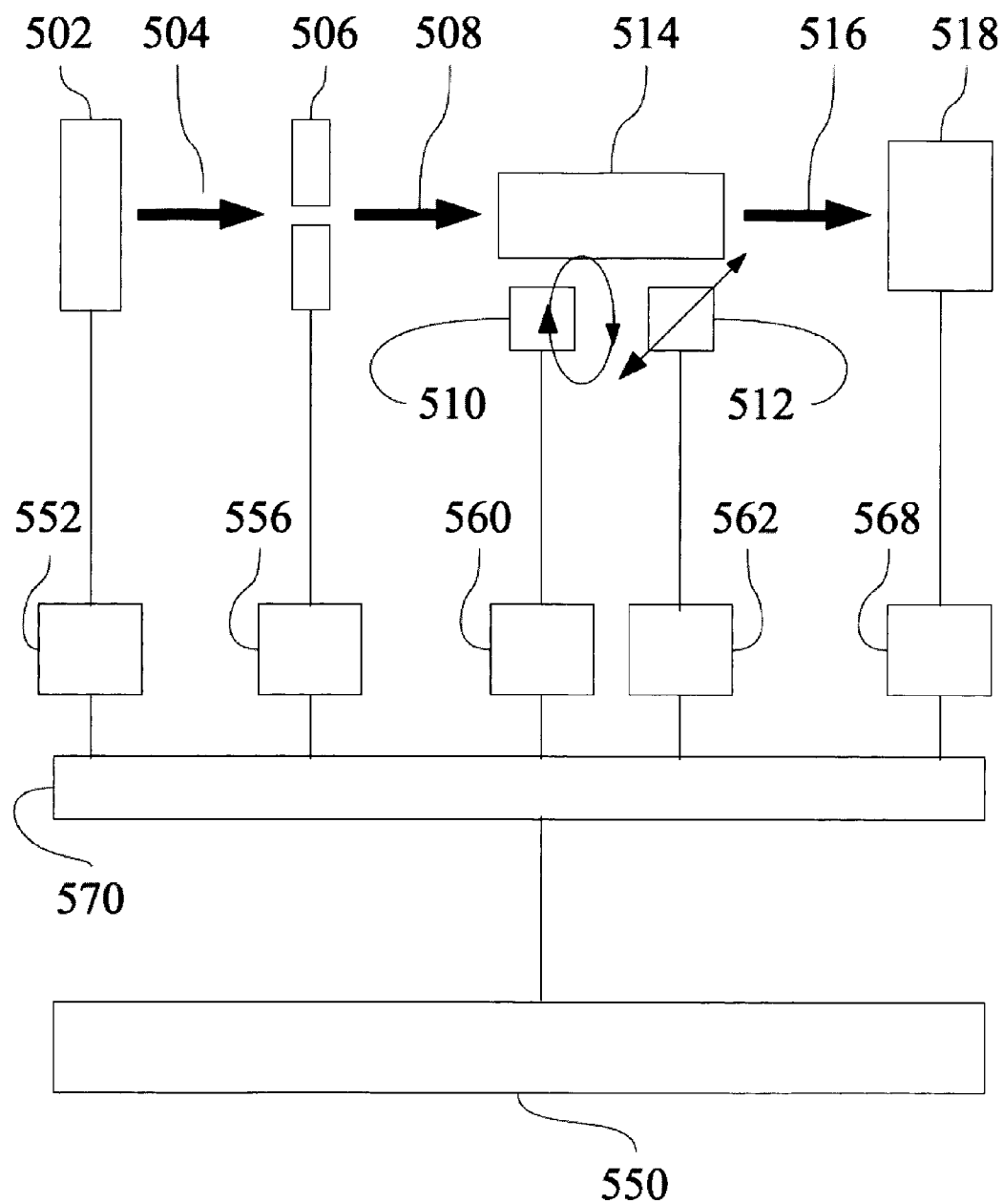
FIG. 5 is a diagram of a modified x-ray computed tomography system according to one embodiment of the present invention.

FIG. 5 illustrates a diagram of another embodiment of the present invention: an x-ray computed tomography system which may be used to collect measurements and to reconstruct at least one image of at least one object of interest. The presented embodiment may reconstruct at least one image of any or several of the following: the average attenuation, the error of the average attenuation, the fluctuation of attenuation, and the error of fluctuation of attenuation of the x-ray absorbance of the object of interest, or any other statistical parameter which may describe the temporal distribution of the collected measurements.

This embodiment uses x-rays to obtain images of at least one object of interest. Other embodiments may use any other penetrating radiation including, but not limited to electron beams, gamma radiation, infrared radiation, infrasound, ion beams, microwaves, radio waves, shock waves, sound, terahertz radiation, ultrasound, ultraviolet radiation, visible light. If other penetrating radiation is used, shaping of the radiation beam may require different elements, including, without limitation, collimator, lenses, electron optics, ion optics and so forth. If other penetrating radiation is used, the radiation may be detected with different detectors sensitive for the actual radiation used in the embodiment, including, without limitation, photon multiplier, CCD camera, piezoelectric detector and so forth.

The system illustrated in FIG. 5 may include a source 502 emitting x-radiation 504. Any suitable source of high energy photons may be used. These alternative sources may include one or more gamma emitting isotopes, or less traditional x-ray emitters (such as x-ray sources using nanotubes as cathode, and so forth). In the exemplary embodiment of FIG. 5 the x-ray source 502 may typically be an x-ray tube connected to an x-ray source controller 552. The x-ray source controller 552 may control the timing and intensity of the emission of the x-ray source.

Adjacent to the x-ray source 502 a collimator 506 may be positioned, through which an x-ray beam 508 may reach the object of interest 514. The collimator 506 may be controlled by a collimator controller 556. The object of interest 514 may be the body or part of the body of a patient or an object or part of an object. As it will be described later, other embodiments may include x-ray sources with different geometry, which may or may not use a collimator.

The portion of the x-ray beam 508 which may pass through or around the object of interest is the x-ray beam 516, which may hit an x-ray detector 518. The detector 518 may contain at least one detector element, which may be sensitive to x-radiation. The detector 518 may include a scintillation element, or a direct conversion material. The x-ray detector 518 in this exemplary embodiment may be a detector array, which may be coupled to an x-ray detector controller 568. In this exemplary embodiment, detector elements of the array may produce electrical signals that represent the intensity of the incident x-ray beams. In this exemplary embodiment, the x-ray detector controller electronics 568 may typically receive analogue electrical signals from the detector 518 and may convert analogue data to digital signals for subsequent processing by a computing means 550. In one embodiment an analogue to digital converter may also be incorporated in the detector, to obtain digital data directly from the detector.

The intensity measurements done by the detector 518 may undergo pre-processing and calibration to condition the data to represent the line integrals of the attenuation coefficients of the scanned object of interest. The obtained projection data may then be filtered and may be used to reconstruct at least one image of the scanned area or part of the scanned area.

The exemplary embodiment presented in FIG. 5 may also involve a rotational subsystem 510 connected to a rotational subsystem controller 560 and a translational subsystem 512 connected to a translational subsystem controller 562. The rotational subsystem 510 and the translational subsystem 512 may allow collection of projections of the object of interest along different directions.

The x-ray source controller 552, the rotational subsystem controller 560, the translational subsystem controller 562, and the x-ray detector controller 568 may all be integrated in a system controller 570, which may be coupled to the computer 550. In this exemplary embodiment, the system controller 570 may command operation of the imaging, data acquisition and preliminary data processing. It is contemplated that an embodiment in which the x-ray source controller 552, the rotational subsystem controller 560, the translational subsystem controller 562, and the x-ray detector controller 568 units are built of several sub-controllers performing parts of the tasks, or are integrated or grouped differently, may also be suitable.

The system controller 570 may perform several tasks connected to the data collection and processing. The system controller 570 may control the x-ray power emitted by the x-ray source 502. It may also command the data acquisition done with the x-ray detector 518. System controller 570 may synchronize the movement generated by the rotational subsystem 510 and the translational subsystem 512 with data collection. It may also carry out various data processing and filtering tasks, it may adjust the dynamic ranges, or perform interleaving the digital image data. In this embodiment, the system controller 570 may include a general purpose or an application specific digital computer, with memory units for storing executable routines, settings, configuration parameters, collected data, and so forth.

As described above, the system controller 570 may command the rotational subsystem 510 and the translational subsystem 512. The rotational subsystem 512 can rotate the x-ray source 502, the collimator 506 and the detector 518 around the object of interest. The translational subsystem 512 enables the linear movement of the x-ray source 502, the collimator 506 and the detector 518. Positioning of the x-ray source 502, collimator 506 and detector 518 might include a gantry, in which case the system controller 570 operates the movement of the gantry. While the system depicted in FIG. 5 illustrates a system that scans in a circular geometry, other geometries, such as for example linear geometry, may also be used.

As will be appreciated by those skilled in the art, instead of utilizing moving components, the imaging system may use stationary source and/or detector. For illustrative purposes only, the imaging equipment may include "third generation" computed tomography scanners, "fourth generation" computed tomography scanners, "fifth generation" computed tomography scanners, or scanners with stationary detector. Other embodiments may include an extended x-ray source and a plurality of detectors, usually located on a ring. The detector ring in such case may include a plurality of distributed detector modules which may be in linear, multi-slice, or other detector arrangements.

In the described embodiment different parts of the imaging equipment may communicate with each other by electric signals, but connections may be done by several other methods. Any method suitable of transferring the necessary information may be used (for example data could also be transferred by the means of optical cable, or wireless connection, and so forth).

The computer 550 may typically be coupled to the system controller. The collected data may be transferred to computer 550, and stored in the digital memory of the computer 550, or any storage device which is part of, or coupled to the computer 550. Any type of memory capable of storing the collected data may be utilized. Moreover, the memory may be located local to the acquisition system, or may include remote components. The computer may be local to the imaging device, or may be remote from it, coupled to the imaging device through a network, or other remote connection. The network may also be connected to a remote client or database. Acquired data, imaging parameters, reconstructed images may be visualized by many methods. These methods may include, but are not limited to, visualizing on screen, printing on paper, slide, or film.

The computer 550 may receive commands, settings and scanning parameters from an operator who controls the imaging system via input devices of the computer. The operator may observe the data or the reconstructed images, set input parameters, initiate imaging, and so forth. The operator may be local to the computer 550, or may be remote from it, coupled to the computer 550 through a network, or other remote connection. Some or all of the data processing described here may be performed remotely.

In the exemplary embodiment of FIG. 5, the reconstructed image may reveal diagnostically important anatomic details about a patient, or visualize the internal structure of any object of interest penetrated by x-rays. The technique may be applied to three-dimensional and to two-dimensional acquisitions as well.

Figure 6:
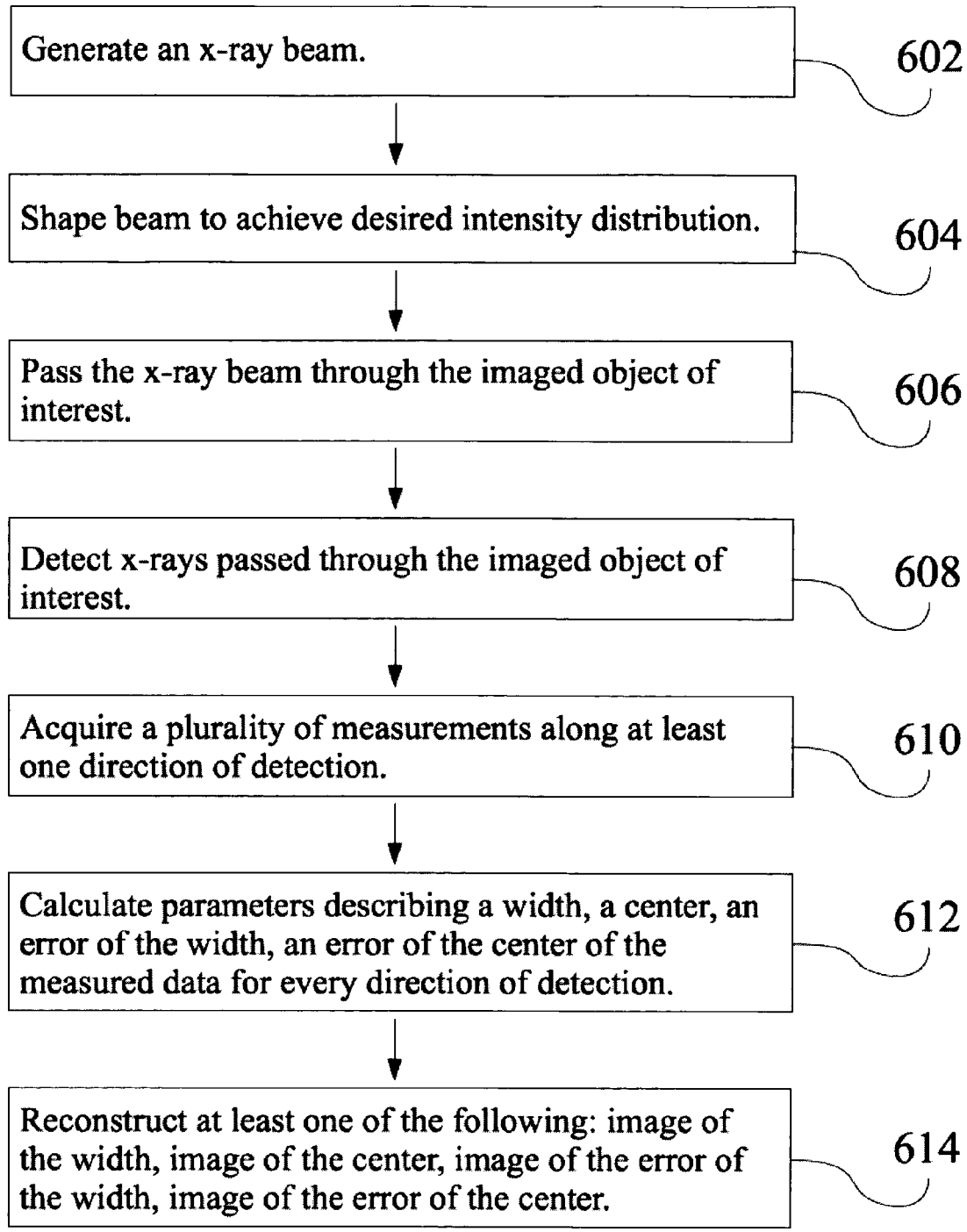
FIG. 6 is a flowchart of data acquisition, processing and image reconstruction in the x-ray computed tomography imaging system represented in FIG. 5.

FIG. 6 is a flowchart including exemplary steps for generating images reconstructed from statistical parameters describing the temporal distribution of the attenuated x-ray radiation collected by the detector using the system described in FIG. 5.

In step 602 x-rays 504 may be generated by the x-ray source 502, shaped by collimator 506 in step 604, and passed through the object of interest 514 in step 606. In step 608 the portion of x-ray 516 which may pass through the object of interest 514 may be detected by the detector 518. In step 610 a plurality of measurements along at least one direction of detection may be collected. In step 612 at least one statistical parameter describing the temporal distribution of the collected plurality of measurements may be calculated. In step 614 the images representing the temporal distribution of x-ray measurements in the object of interest may be reconstructed. In step 614 images of the error of the statistical parameters may also be calculated.

As will be appreciated by those skilled in the art, intensity readings (or other readings related to intensity) by the detector 518 may be subject to fluctuations. These fluctuations may come from two sources: random noise of the measurement, and real changes in the attenuation of the x-rays 508 inside the object of interest 514. Random noise may come from the Poisson shot noise of the detection, from electronic noise of the detector, or attached electronics parts, etc. Random noise contains no information about the object of interest 518. Fluctuations arising from real attenuation changes of the object of interest 514 may carry important information about the movements of the object of interest.

Figure 7:
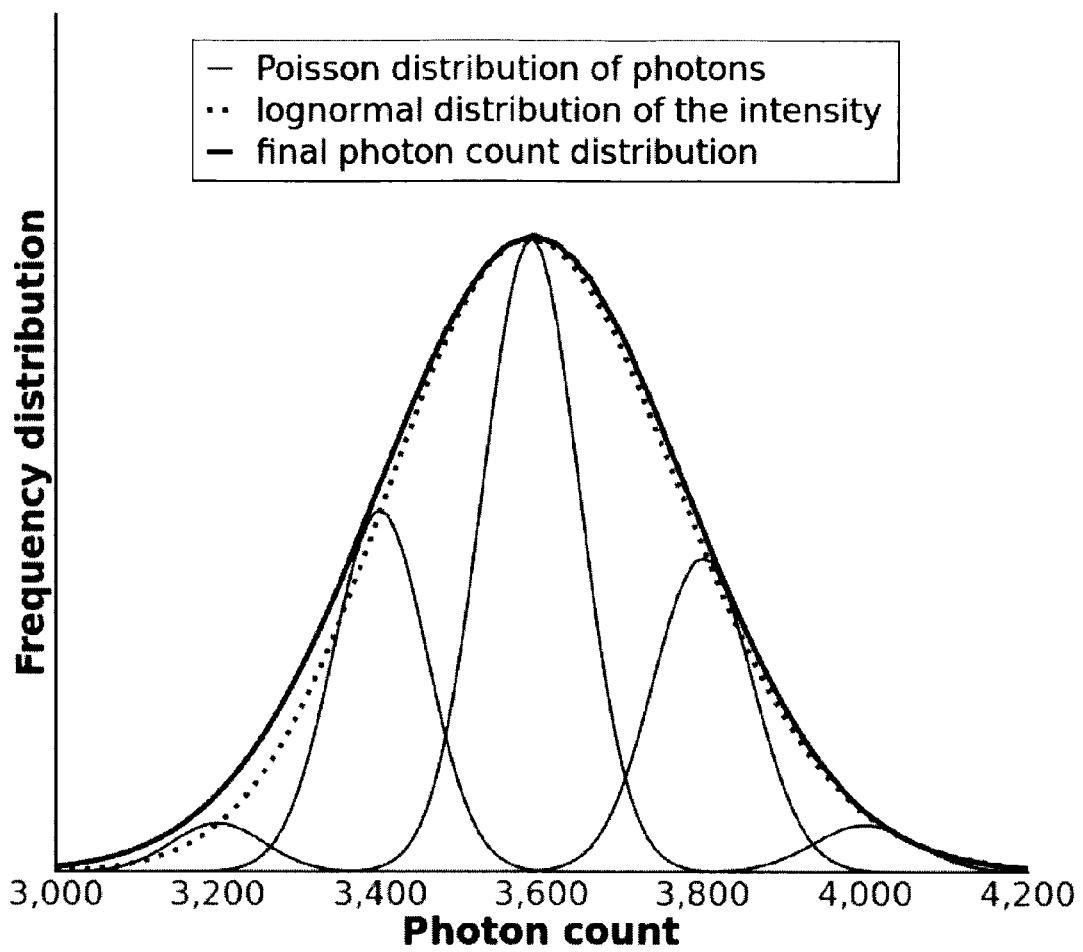
FIG. 7 is an exemplary illustration of the detector noise, intensity fluctuations due to changes in the attenuation of the penetrating radiation, and the resulting distribution of detector readings.

FIG. 7 illustrates how the distribution of the random noise and distribution of the fluctuations of the object of interest may determine the distribution of the detector readings. Fluctuations originating in the object of interest may be separated from random noise, and a new type of image representing the fluctuations of the object may thus be created.

The described exemplary embodiment of FIG. 5 may separate random noise which may be dominated by Poisson shot noise from attenuation fluctuations which may follow normal distribution. Other embodiments may represent the fluctuations of the measured intensities without separating the random noise from fluctuations reflecting attenuation changes. These images may also contain the information about the attenuation fluctuations. In many cases such images may be just as usable as those images which were obtained after the separation of the random fluctuations and those originating in the object of interest. It is contemplated, however, that those images which are obtained after extraction of the random noise from the fluctuations may be of a substantially higher quality.

The above distributions may be considered in this exemplary embodiment for the following reasons. The sum of several random variables with finite means and variances approaches normal distribution as the number of variables increases. Because of this, normal distribution may be commonly encountered in biological and physical systems. Poisson noise is typical for particle counting measurements.

Less frequently than the distributions taken in account in this embodiment, other distributions may also be of interest. The actual distributions of the random noise and attenuation fluctuations may depend on details of the embodiment, type of penetrating radiation, object of interest, and so forth. Based on the present disclosure, embodiments in which the separated random noise and/or attenuation fluctuations follow other distributions may also be constructed by the person skilled in the art.

The attenuation of x-rays in an absorber may be described by exponential formula (1):

$$I=I_0 \cdot \text{Exp}[-D] \qquad (8)$$

where I denotes the expected value of the number of x-ray photons after the absorber, $I_0$ denotes the expected value of the number of x-ray photons before the absorber, D denotes the x-ray density of the absorber. Exp[ . . . ] denotes the e-based exponential function.

If the x-ray beam crosses several absorbers with x-ray densities $D_i$ each, the combined density D of the series of absorbers may be calculated as the sum of the density of the individual parts:

$$D=\Sigma_i D_i \qquad (9)$$

where i may be 1, 2, 3, . . . indexing the absorbers, and $\mu_i$ represents summation for all i-s. The densities $D_i$ may represent the x-ray densities of volume elements (voxels) of an object of interest. If the densities $D_i$ vary following normal distributions with expected values $E(D_i)$ and variances Var $(D_i)$, then D will also follow a normal distribution with an expected value $E(D)$ and variance $\text{Var}(D)$. $E(D)$ and variance $\text{Var}(D)$ determined by the sum of the expected values and the sum of the variances of the $D_i$ densities, respectively:

$$E(D)=\Sigma_i E(D_i), \qquad (10)$$

$$\text{Var}(D)=\Sigma_i \text{Var}(D_i). \qquad (11)$$

To determine experimentally the x-ray density D of an object of interest, the x-ray intensities I may be measured. The result of the intensity measurement may typically be a photon number reading: k. Making a plurality of photon number detections may reveal that the photon numbers k fluctuate. These fluctuations may come from two sources: random noise of the measurement and real changes in the x-ray density D.

If the x-ray density D follows normal distribution, the intensity I will follow lognormal distribution. In this embodiment it will be assumed that the random noise of the detection is determined by the Poisson shot noise of photon counting. Taking into account both sources of fluctuations the following expressions may be obtained for the expected value and variance of the detected photon numbers k:

$$E(k)=I_0 \cdot \text{Exp}[\text{Var}(D)/2-E(D)], \qquad (12)$$

$$\text{Var}(k)=I_0 \cdot \text{Exp}[\text{Var}(D)/2-2 \cdot E(D)] \cdot (\text{Exp}[D]-I_0 \cdot \text{Exp}[0.5 \cdot \text{Var}(D)]+I_0 \cdot \text{Exp}[1.5 \cdot \text{Var}(D)]) \qquad (13)$$

If the expected value $E(k)$ and variance $\text{Var}(k)$ of the photon counts k are determined experimentally, the expected value $E(D)$ and the variance $\text{Var}(D)$ of the density D may be calculated by solving the above equations:

$$E(D)=\text{Log}[I_0 \cdot \text{Sqrt}[\text{Var}(k)-E(k)+E(k)^2]/E(k)^2], \qquad (14)$$

$$\text{Var}(D)=2 \cdot \text{Log}[\text{Sqrt}[\text{Var}(k)-E(k)+E(k)^2]/E(k)] \qquad (15)$$

where Log[ . . . ] denotes the natural (e-based) logarithm, Sqrt[ . . . ] denotes the square root function.

An estimation of the expected value $E(k)$ of the photon number k alone may be used to determine the density D, only if the variance of D is zero. If the x-ray density D varies, both the expected value $E(D)$ and the variance $\text{Var}(D)$ of the density D may be calculated from the expected value $E(k)$ and variance $\text{Var}(k)$ of the photon counts k. Depending on the fluctuations, an x-ray density determined from the expected value $E(k)$ of the photon numbers may differ significantly from the expected value $E(D)$ of the density. The presented embodiment thus may yield a more accurate image of the object of interest than methods of the prior art which determine an estimation only for the expected value of the photon counts.

The expected value $E(k)$ and variance $\text{Var}(k)$ of the photon counts are parameters that describe the theoretical distribution of the photon counts k. These parameters can not be determined directly, but they can be estimated from measurements.

The presented embodiment may make a plurality (n) of photon count readings and may calculate an estimation for both the expected value $E(k)$ and variance $\text{Var}(k)$ of the photon counts k. The estimations for the expected value $E(k)$ and for the variance $\text{Var}(k)$ may be used to calculate an estimation of the expected value $E(D)$ and the variance $\text{Var}(D)$ of the density D. Estimating the expected value $E(D)$ and the variance $\text{Var}(D)$ for a plurality of projection directions may be used to reconstruct three dimensional images of the expected value $E(D_i)$ and variance $\text{Var}(D_i)$ of the x-ray density of the object of interest.

Figure 8:
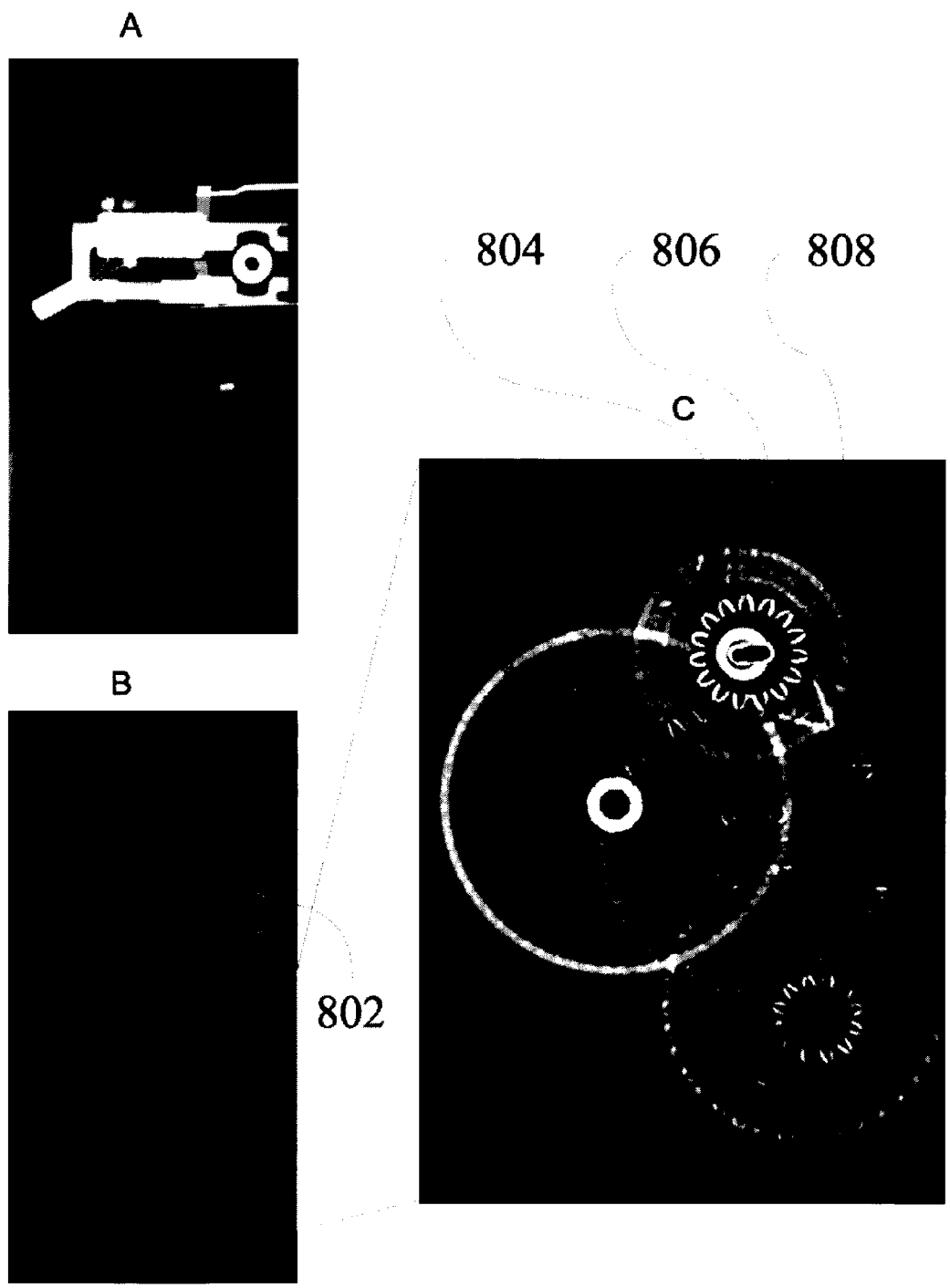
FIG. 8A is an exemplary projection average density image of the wheels of a clock obtained with the embodiment described in FIG. 5.
FIG. 8B is an exemplary projection variance density image of the wheels of a clock obtained with the embodiment described in FIG. 5.
FIG. 8C is a magnification of a portion of FIG. 8 B.

FIG. 8 includes projection images of moving cogged wheels of a clock. These images were recorded along a fixed projection angle using the system described in FIG. 5. FIG. 8A illustrates the average density image $E(D)$. FIG. 8B shows the variance image $\text{Var}(D)$. At first sight, in FIG. 8B the fastest wheel 802 moving the whole mechanics of the clock may be seen. FIG. 8C magnifies a smaller part of the variance image $\text{Var}(D)$ to illustrate the dynamic range and the quality of the image. Since the mechanics moving the second 804, minute 806, and hour 808 fingers move at different speed, the dynamic range of these movements is broad.

FIG. 9 includes projection images of the chest of a living frog. These images were recorded along a fixed projection angle using the system described in FIG. 5. FIG. 9A illustrates the average density image $E(D)$ of the frog. FIG. 9B shows the variance image $\text{Var}(D)$ of the same part of the frog. Frogs have very weak soft tissue contrast, and the average density image practically only shows the bones. In the variance image the lung (902), the heart (904) and the aorta (906) are highlighted. The two valves (908) of the frog's heart appear as two bright short lines. The back of the tongue or the throat (910) of the frog also moves as it is breathing.

FIG. 10 includes projection images of that part of a snake that contains the heart. These images were recorded along a fixed projection angle using the system described in FIG. 5. FIG. 10A illustrates the average density image $E(D)$ of part of the snake. FIG. 10B shows the variance image $\text{Var}(D)$ of the same part of the animal. While the average image mainly shows the bones, the elongated heart (1010) of the snake is visualised in the variance image.

In many applications it may be useful to determine the error of the reconstructed images of the expected value $E(D_i)$ and variance $Var(D_i)$ of the voxel x-ray densities. Error images may hold important information, including, without limitation, for optimization of data acquisition, for efficient image analysis, denoising, or automatic shape recognition.

The images representing $E(D_i)$ and $Var(D_i)$ were reconstructed from the expected value $E(k)$ and the variance $Var(k)$ which were estimated from the photon numbers. To estimate the error of the images $E(D_i)$ and $Var(D_i)$, first it may be needed to give an estimation for the error of the expected value $E(k)$ and the error of the variance $Var(k)$ of the detected photon numbers.

To estimate the error of $E(k)$ and $Var(k)$ any statistical method (such as jackknifing, bootstrapping, and so forth) may be used which allows a reasonably accurate guess of the errors. For normal distributions the error of the estimation of the expected value and of the variance can be easily calculated:

$$Err(E(k))=Var(k)/Sqrt[n], \quad (16)$$

$$Err(Var(k))=0.71 \cdot Var(k)/Sqrt[n], \quad (17)$$

where $Err(E(k))$ represents the error of the estimation of the expected value $E(k)$, $Err(Var(k))$ represents the error of the estimation of the variance $Var(k)$, n denotes the number of the photon count measurements. Although the above error estimations were derived for normal distributions, the estimation method is robust, and the error estimations calculated based on the above formula may give an adequate estimation of the error of $E(k)$ and $Var(k)$ for other distributions as well.

The presented exemplary embodiment, may use the above formula for the estimation of the errors $Err(E(k))$ and $Err(Var(k))$. The expressions for the errors of the expected value $E(D)$ and the variance $Var(D)$ of the density D may be derived from the expressions for $E(D)$ and $Var(D)$. After simplifying the expressions, $Err(E(D))$ and $Err(Var(D))$ may be calculated from the errors of the expected value $E(k)$ and variance $Var(k)$ of the photon counts k in the following way:

$$Err(E(D))=(E(k)^2-1.855 \cdot E(k)+2 \cdot Var(k)) \cdot Var(k)/(Sqrt[n] \cdot E(k) \cdot (E(k)^2-E(k)+Var(k))), \quad (18)$$

$$Err(Var(D))=(1.71 \cdot E(k)-2 \cdot Var(k)) \cdot Var(k)/(Sqrt[n] \cdot E(k) \cdot (E(k)^2-E(k)+Var(k))). \quad (19)$$

Other embodiments may use other statistical methods such as jackknifing or bootstrapping which may give a better estimation of the errors, but may also be more computation-intensive.

As described above, the presented embodiment may use a plurality of detector photon count readings k to calculate an estimation for (1) the expected value $E(D)$, (2) the variance $Var(D)$, (3) the error of the expected value $Err(E(D))$, and (4) the error of the variance $Err(Var(D))$ of the density D. These four quantities may be determined for a plurality of projection angles, which may allow reconstructing four different three dimensional images of the object of interest: the mean x-ray density image, the x-ray density variance (fluctuation) image, the image representing the error of the x-ray density variance (fluctuation), and image representing the error of the mean x-ray density.

The exemplary embodiment described herein may use weighted filtered back projection to determine the above images. Several other method exist that may be used to reconstruct three dimensional images from their projections. Other embodiments may use other reconstruction methods.

In accordance with the presented exemplary embodiment, the expected value $E(D)$, the variance $Var(D)$, the square of the error of the expected value $Err(E(D))$, and the square of the error of the variance $Err(Var(D))$ may be processed by a three dimensional reconstruction algorithm. The contemplated algorithm may include a series of weighting, filtering and back projection steps for each projection measurement over the reconstruction volume. Weighting of the projection data may be performed by an element-by-element multiplication with an array containing the weighting factors. The filtering step may use a series of convolutions to decorrelate image data points. In the back projection step the projection measurements may be added to all voxels along the projection line. Different x-ray beam geometries may be taken into account through the use of weighting factors in the back projection. The exemplary embodiment may process the square of the errors $Err(E(D))$ and $Err(Var(D))$ obtained from the projections, thus an image that represents the square of the errors in the voxels may be obtained. To represent the errors, a square root may be calculated voxel by voxel.

The exemplary embodiment described here, thus may calculate the expected value $E(D_i)$, the variance $Var(D_i)$, the error of the expected value $Err(E(D_i))$, and the error of the variance $Err(Var(D_i))$ for the $D_i$ densities of the volume elements of the object of interest.

The expected value image reconstructed using the presented embodiment may be more accurate than images obtained by previous techniques. This, in many cases may be an important advancement itself. The variance image may reflect the fluctuations in the x-ray absorbance, a new modality that may be used for the visualization of movements inside the object of study. The new modality may bring new contrast schemes as well, which may allow the visualization of structures which were not previously resolvable. The more accurate measurement-based reconstruction of the error of the expected value and variance images may be very useful in many cases. These error images may be used in the optimization of image acquisition parameters, decision making about the reacquisition of images of insufficient quality, diagnostic decision making, computer aided detection, identification of regions of interest, digital image processing, image noise reduction, averaging of images, and so forth.

As will be appreciated by those skilled in the art, the exemplary embodiments of the measuring devices and methods described above may involve extensive computer calculations. These calculations may include a listing of computer code containing executable instructions. This listing (program) may be embodied in any computer-readable information storage device, for use by or in connection with a system which can execute the instructions. The processing may be done local to the acquisition or local to the storage of the acquired data. Alternatively, some or all the calculations may be performed remotely. The computer-readable information storage device may be any means that can contain, store, communicate, propagate, transmit or transport information. The usable devices may use electronic, magnetic, optical, electromagnetic, mechanic, nanotechnology-based media, but are not limited to these.

The presented embodiments are described here as exemplary systems only. It should be noted that the presented systems and methods are in no way limited to the actual arrangements described, or the use of x-radiation or electron beams.

Other embodiments can be envisioned for acquiring and processing the attenuation of penetrating radiation to obtain at least one of the following images: the mean attenuation image, its error, the image of the deviation of the attenuation, and its error.

Glossary of Technical Terms

Bootstrapping—Bootstrapping is a general purpose re-sampling method for statistical inference.

Expected value—The expected value (also called mean) of a random variable is the integral of the random variable with respect to its probability measure. For discrete variables this is the probability-weighted sum of the possible values.

Fifth generation CT scanner—A fifth generation computed tomography scanner is a CT scanner which uses a stationary detector ring and an X-ray tube moving on a circular path outside the detector ring.

Fourth generation CT scanner—A fourth generation computed tomography scanner is a CT scanner which uses a stationary detector ring and an X-ray tube moving on a circular path inside the detector ring.

Jackknifing—Jackknifing is a statistical method that calculates standard error of a statistic estimate by systematically recomputing multiple times the statistic estimate leaving out one observation from the sample set.

Projection—A projection may be defined as a shadow image of the attenuation of the object of interest recorded under one single angle of view.

Scan—A scan comprises of a set of projections recorded under different angles of view which allow the reconstruction of the internal structure of at least a part of the object of interest.

Shock wave—A shock wave is an abrupt propagating disturbance.

Shot noise—Shot noise refers to the statistical fluctuations of counting a finite number of particles that carry energy (photons, electrons, etc.).

Third generation CT scanner—A third generation computed tomography scanner is a CT scanner in which a fan-beam projection allows the simultaneous measurement of the entire patient cross-section.

Variance—The variance of a random variable is the expected value of the square of the deviation of that variable from its expected value. Variance measures the amount of variation within the values of the variable.

x-ray density—The x-ray density (also called x-ray absorbance) of an absorber is defined as $D=\text{Log}[I_0/I]$, where I is the x-ray intensity that has passed through the absorber, $I_0$ is the intensity of the x-ray before it enters the absorber, $\text{Log}[\ldots]$ denotes the natural (e-base) logarithm. Alternatively, density can also be defined as $D=\text{Log}_{10}[I_0/I]$, where $\text{Log}_{10}[\ldots]$, denotes the 10-base logarithm function.

We claim:

1. A method for imaging an object of interest using penetrating radiation, comprising:
    (a) positioning a source of penetrating radiation and a radiation detector externally of the object of interest and with the object of interest positioned therebetween;
    (b) repeatedly measuring the penetrating radiation generated by the source of penetrating radiation and passing through the object of interest along each of at least one linear path extending from the source of penetrating radiation to the radiation detector and intersecting the object of interest, by: (i) exposing the object of interest to the penetrating radiation thereby allowing the radiation to pass through said object, and (ii) detecting the penetrating radiation which passes through the object of interest along each of the at least one linear path, thereby to generate a plurality of measurements for each of the at least one linear path;
    (c) processing the plurality of measurements for each of the at least one linear path to obtain at least one statistical parameter capable of describing a width of a temporal distribution of the plurality of measurements for each of the at least one linear path, and
    (d) reconstructing the image of the object of interest based on the at least one parameter describing the distribution of the plurality of measurements, thereby obtaining images of the object of interest.

2. The method of claim 1, characterized in that the penetrating radiation is detected with a detector and said measurements are obtained from signals generated by said detector.

3. The method of claim 1, characterized in that the at least one statistical parameter is capable of describing an error of the width of the temporal distribution of the plurality of measurements.

4. The method of claim 1, characterized in that the at least one statistical parameter is selected from a variance, a standard deviation, expected deviation, average absolute deviation or a moment of the distribution of the plurality of measurements obtained using the penetrating radiation.

5. The method of claim 1, characterized in that the method further includes obtaining at least one other statistical parameter capable of describing the center of the temporal distribution of the plurality of measurements for each direction of detection, and reconstructing another image of the object of interest based on the at least one other parameter.

6. The method of claim 5, characterized in that the at least one statistical parameter includes a statistical parameter capable of describing an error of the center of the temporal distribution of the plurality of measurements.

7. The method of claim 5, characterized in that the at least one other statistical parameter is selected from a mean, an average, an expected value, a median or a mode.

8. The method of claim 1, characterized in that the penetrating radiation is selected from electron beams, gamma radiation, infrared radiation, infrasound, ion beams, microwaves, radio waves, shock waves, sound, terahertz radiation, ultrasound, ultraviolet radiation, visible light, or x-rays.

9. The method of claim 1, characterized in that said plurality of measurements is selected from a plurality of intensity measurements, attenuation measurements and a field strength measurements.

10. An image processing method for determining relative movement of structures within an object of interest, comprising:
    (a) positioning a source of penetrating radiation and a radiation detector externally of the object of interest and with the object of interest positioned therebetween;
    (b) repeatedly measuring a penetrating radiation generated by the source of penetrating radiation and passing through the object of interest along each of at least one linear path extending from the source of penetrating radiation to the radiation detector and intersecting the object of interest, by: (i) passing the penetrating radiation through the object of interest, and (ii) detecting the penetrating radiation which passes through the object of interest along each of the at least one linear path, thereby to generate a plurality of measurements for each of the at least one linear path;
    (c) processing the plurality of measurements for each of the at least one linear path to obtain at least one parameter which describes a fluctuation of the plurality of measurements for each of the at least one linear path, and
    (d) reconstructing an image of the object of interest based on the at least one parameter, wherein said reconstructed image based on the fluctuation of the plurality of measurements provides information on the relative movement of structures within the object of interest.

11. The image processing method of claim 10, characterized in that the at least one statistical parameter which describes a fluctuation of the plurality of measurements is a statistical parameter capable of describing the width of the temporal distribution of the plurality of measurements for each direction of detection.

12. The image processing method of claim 10, characterized in that the at least one statistical parameter is selected from a variance, a standard deviation, expected deviation, average absolute deviation or a moment of the distribution of the plurality of measurements obtained using the penetrating radiation.

13. The image processing method of claim 10, characterized in that the penetrating radiation is detected with a detector and said measurements are obtained from signals generated by said detector.

14. The image processing method of claim 10, characterized in that the penetrating radiation is selected from electron beams, gamma radiation, infrared radiation, infrasound, ion beams, microwaves, radio waves, shock waves, sound, terahertz radiation, ultrasound, ultraviolet radiation, visible light, or x-rays.

15. A system for reconstructing an image of an object of interest comprising:
(a) a source configured to emit penetrating radiation positioned externally of the object of interest;
(b) a detector sensitive to said penetrating radiation positioned externally of the object of interest and opposite said source with respect to the object of interest, said detector configured to repeatedly measure the penetrating radiation generated by the source and passing through the object of interest along each of at least one linear path extending from the source of penetrating radiation to the radiation detector and intersecting the object of interest;
(c) a processor having at least one algorithm that calculates at least one statistical parameter capable of describing a width of a temporal distribution of the plurality of measurements for each of the at least one linear path; and
(d) an image reconstruction processor that reconstructs the image of the object of interest based on the at least one parameter describing the distribution of the plurality of measurements.

16. The system of claim 15, characterized in that said system further comprises means for holding the object of interest in a position relative to the source of penetrating radiation and the detector.

17. The system of claim 15, characterized in that said system further comprises rotational and translational means linked to the holding means for allowing collection of the substantially emitted penetrating radiation through the object of interest along a plurality of directions of detection.

18. The system of claim 15, characterized in that said system further includes a system controller means linked to said detector, said data processor means and said image reconstruction processor means for controlling the substantially emitted penetrating radiation, the production of measurements, and the processing and reconstruction of the measurements.

19. The system of claim 18 further comprising a computer linked to the system controller means.

20. The system of claim 19 characterized in that said computer includes input means for controlling the imaging system and means for storing the plurality of measurements.

21. The system of claim 15, characterized in that said penetrating radiation is selected from electron beams, gamma radiation, infrared radiation, infrasound, ion beams, microwaves, radio waves, shock waves, sound, terahertz radiation, ultrasound, ultraviolet radiation, visible light, or x-rays.

22. The system of claim 15, characterized in that said system is an environmental transmission electron microscope system, and wherein said penetrating radiation is electron beams.

23. The system of claim 15, characterized in that said system is an x-ray apparatus, and wherein the penetrating radiation is x-rays.

24. The system of claim 15, characterized in that the processor has another algorithm for calculating a statistical parameter capable of describing an error of the width of the temporal distribution of the plurality of measurements.

25. The system of claim 15, characterized in that the processor includes another algorithm for calculating a statistical parameter capable of describing a center of the temporal distribution of the plurality of measurements.

26. The system of claim 15, characterized in that the processor includes another algorithm for calculating a statistical parameter capable of describing an error of a center of the temporal distribution of the plurality of measurements.

27. The system of claim 15, characterized in that said measurements are obtained from signals generated by said detector.

* * * * *